US012733820B2

(12) United States Patent
Bikia et al.

(10) Patent No.: US 12,733,820 B2
(45) Date of Patent: Sep. 15, 2026

(54) SYSTEM AND METHODS FOR REAL TIME NONINVASIVE ESTIMATION OF CARDIOVASCULAR PARAMETERS USING MACHINE LEARNING

(71) Applicant: ECOLE POLYTECHNIQUE FEDERALE DE LAUSANNE (EPFL), Lausanne (CH)

(72) Inventors: Vasiliki Bikia, Lausanne (CH); Stamatia Pagoulatou, Lausanne (CH); Nikolaos Stergiopulos, Preverenges (CH)

(73) Assignee: Ecole Polytechnique Federale De Lausanne (EPFL), Lausanne (CH)

( * ) Notice: Subject to any disclaimer, the term of this patent is extended or adjusted under 35 U.S.C. 154(b) by 937 days.

(21) Appl. No.: 17/753,055

(22) PCT Filed: Aug. 14, 2020

(86) PCT No.: PCT/IB2020/057656
§ 371 (c)(1),
(2) Date: Feb. 16, 2022

(87) PCT Pub. No.: WO2021/033097
PCT Pub. Date: Feb. 25, 2021

(65) Prior Publication Data

US 2022/0287640 A1 Sep. 15, 2022

Related U.S. Application Data

(60) Provisional application No. 63/058,405, filed on Jul. 29, 2020, provisional application No. 62/889,535, filed on Aug. 20, 2019.

(51) Int. Cl.
*A61B 5/02* (2006.01)
*A61B 5/00* (2006.01)
(Continued)

(52) U.S. Cl.
CPC ............ *A61B 5/02* (2013.01); *A61B 5/02007* (2013.01); *A61B 5/02125* (2013.01);
(Continued)

(58) Field of Classification Search
None
See application file for complete search history.

(56) References Cited

U.S. PATENT DOCUMENTS 6,254,544 B1 * 7/2001 Hayashi ................ A61B 5/022 600/500
6,428,482 B1 * 8/2002 Sunagawa .......... A61B 5/02116 600/490
(Continued)

FOREIGN PATENT DOCUMENTS

EP 1055394 A2 11/2000
WO WO-2021033097 A1 2/2021
(Continued)

OTHER PUBLICATIONS

International Search Report & Written Opinion dated Apr. 11, 2024 in Int'l PCT Patent Appl. Serial No. PCT/IB2023/061658 (131001).
(Continued)

*Primary Examiner* — Michael R Bloch
(74) *Attorney, Agent, or Firm* — Greenberg Traurig, LLP; Christopher C. Bolten; Robert D. Ward

(57) ABSTRACT

Systems and methods are provided for that use noninvasively measured physiologic parameters to predict in real time noninvasively unobservable cardiovascular parameters by employing a one-dimensional arterial tree numerical model calibrated with representative patient data. The numerical model further may be trained and calibrated on a larger database that includes synthetic data using machine-
(Continued)

learning algorithms to provide a robust generalized estimator for multiple cardiovascular and hemodynamic parameters.

10 Claims, 11 Drawing Sheets

(51) Int. Cl.

| | |
|---|---|
| ***A61B 5/021*** | (2006.01) |
| ***A61B 5/022*** | (2006.01) |
| ***A61B 5/024*** | (2006.01) |
| ***A61B 5/029*** | (2006.01) |
| ***A61B 5/318*** | (2021.01) |
| ***A61B 7/02*** | (2006.01) |
| ***G16H 50/20*** | (2018.01) |
| ***G16H 50/70*** | (2018.01) |

(52) U.S. Cl.

CPC .............. *A61B 5/022* (2013.01); *A61B 5/024* (2013.01); *A61B 5/029* (2013.01); *A61B 5/318* (2021.01); *A61B 5/7221* (2013.01); *A61B 5/7267* (2013.01); *A61B 5/7278* (2013.01); *A61B 7/02* (2013.01); *G16H 50/20* (2018.01); *G16H 50/70* (2018.01)

(56) References Cited

U.S. PATENT DOCUMENTS

| | | | | |
|---|---|---|---|---|
| 6,740,045 | B2 * | 5/2004 | Amano | A61B 5/681 600/501 |
| 8,602,997 | B2 * | 12/2013 | Banet | A61B 5/02133 600/500 |
| 2010/0016736 | A1 * | 1/2010 | Hahn | A61B 5/02125 600/485 |
| 2010/0317976 | A1 * | 12/2010 | Chelma | A61B 5/021 600/485 |
| 2011/0263989 | A1 * | 10/2011 | Mukkamala | A61B 5/02125 600/485 |
| 2013/0184595 | A1 * | 7/2013 | Mukkamala | A61B 5/7278 600/500 |
| 2013/0310700 | A1 * | 11/2013 | Wiard | A61B 5/318 600/500 |
| 2014/0249442 | A1 * | 9/2014 | Banet | A61B 5/02028 600/526 |
| 2015/0324962 | A1 * | 11/2015 | Itu | G16H 30/40 382/130 |
| 2017/0347899 | A1 * | 12/2017 | Bhushan | A61B 5/6833 |
| 2018/0020931 | A1 * | 1/2018 | Shusterman | A61N 1/3627 600/483 |
| 2018/0358119 | A1 * | 12/2018 | Bhushan | G16H 40/63 |
| 2020/0323440 | A1 | 10/2020 | Vule et al. | |
| 2021/0353164 | A1 | 11/2021 | Chegani et al. | |

FOREIGN PATENT DOCUMENTS

| | | | |
|---|---|---|---|
| WO | WO-2024033793 | A1 | 2/2024 |
| WO | WO-2024110829 | A1 | 5/2024 |

OTHER PUBLICATIONS

Berkenstadt, et al. "Stroke Volume Variation as a Predictor of Fluid Responsiveness in Patients Undergoing Brain Surgery," Anesthesia & Analgesia, vol. 92(4):984-989 (Apr. 2001).

Bikia et al., "Determination of Aortic Characteristics Impedance and Total Arterial Compliance From Regional Pulse Wave Velocities Using Machine Learning: An in-silico Study," Front. Bioeng. Biotechnol., vol. 9—p. 649866 (May 2021).

Bikia, et al., Estimation of Left Ventricular End-Systolic Elastance From Brachial Pressure Waveform via Deep Learning, Frontiers In Bioengineering and Biotechnology, 9(754003) (Oct. 2021).

Bikia, et al., Estimation of Patient-Specific Central Hemodynamic Indices From Brachial Pressure and Pulse Wave Velocity, 25th Congress of the European Society of Biomechanics, Vienna, Austria (Jul. 2019).

Bikia, et al., Noninvasive Cardiac Output and Central Systolic Pressure From Cuff-Pressure and Pulse Wave Velocity, IEEE Journal of Biomedical and Health Informatics, IEEE, 24(7):1968-1981 (Jul. 2020).

Bikia, et al., Statistical Learning For Estimating Central Systolic Blood Pressure Using Data From a Simulated Arterial Tree Model, 25th Congress of the European Society of Biomechanics, Vienna, Austria (Jul. 2019).

Chemla, D. et al., "Total arterial compliance estimated by stroke volume-to -aortic pulse pressure ratio in humans," Am. J. Physiol. Heart and Circulatory Physiol., vol. 274(2):H500-H505 (Feb. 1998).

Chen, et al., Coupled Systolic=Ventricular and Vascular Stiffening With Age. Implications for Pressure Regulation and Cardiac Reserve in the Elderly, Journal of the American College of Cardiology, 32(5):1221-1227 (Nov. 1998).

Chen, et al., Noninvasive Single-Beat Determination of Left Ventricular End-Systolic Elastance in Humans, Journal of the American College of Cardiology, 38(7):2028-2034 (Dec. 2001).

De Simone et al., "Stroke Volume/Pulse Pressure Ratio and Cardiovascular Risk in Arterial Hypertension," Hypertension, vol. 33(3):800-805, (Mar. 1999).

Feldman, et al., Acute Cardiovascular Effects of OPC-18790 in Patients With Congestive Heart Failure, Circulation, 93(3):474-483 (Feb. 1996).

Friedman, Jerome H., Greedy Function Approximation: A Gradient Boosting Machine, IMS Reitz Lecture (Feb. 1999).

Haluska, et al., Influence of Arterial Compliance on Presence and Extent of Ischaemia During Stress Echocardiography, Heart, 92(1):40-43 (Jan. 2006).

Haluska, et al., Influence of Cardiovascular Risk Factors on Total Arterial Compliance, Journal of the American Society of Echocardiography, 21(2):123-128 (Feb. 2008).

Ibrahim, et al., Cuffless blood pressure monitoring from a wristband with calibration-free algorithms for sensing location based on bio-impedance sensor array and autoencoder, Scientific Report, 12(1):319 (Jan. 2022).

International Search Report & Written Opinion dated Jan. 9, 2024 in Int'l PCT Patent Appl. Serial No. PCT/IB2023/057976 (101001).

International Search Report & Written Opinion dated Oct. 20, 2020 in Int'l PCT Patent Appl. Serial No. PCT/IB2020/057656 (0710).

Jhanji, S et al., "Cardiac output monitoring: basic science and clinical application," Anesthesia, vol. 63(2):172-181, (2008).

Kroeker et al., "Comparision of Simultaneously Recorded Central and Peripheral Arterial Pressure Pulses During Rest, Exercise and Tilted Position in Man," Circulation Research, vol. 3(6):623-632 (Nov. 1955).

Laurent et al., "Expert consensus document on arterial stiffness: methodological issues and clinical applications," European Heart Journal, vol. 27(21):2588-2605, (Sep. 2006).

Learoyd, et al., Alterations With Age in the Viscoelastic Properties of Human Arterial Walls, Circulation Research, 18(3):278-292 (Mar. 1966).

Ledoux, D. et al., "Effects of perfusion pressure on tissue perfusion in septic shock," Critical Care Medicine, vol. 28(8):2729-2732 (Aug. 2000).

Lees et al., "Clinical review: Goal-directed therapy in high risk surgical patients," Crit Care, vol. 13(5): 231 (pp. 1-8), (Oct. 2009).

Liaw A., et al., "Classification and Regression By RandomForest," R News, Dec. 2002, vol. 2/3, pp. 18-22.

Liu, et al., Patient-Specific Oscillometric Blood Pressure Measurement, IEEE Trans. Biomed. Eng., 63(6):1220-1228 (Jun. 2016).

MacKenzie, et al., Assessment of Arterial Stiffness in Clinical Practice, Q.J. Med., 95(2):67-74 (Feb. 2002).

McKendry et al., "Randomised controlled trial assessing the impact of a nurse delivered, flow monitored protocol for optimisation of circulatory status after cardiac surgery," BMJ, vol. 329(7460):258 (Jul. 2004).

Milnor, William, Arterial Impedance As Ventricular Afterload, Circulation Research, 36(5):565-570 (May 1975).

(56) References Cited

OTHER PUBLICATIONS

Mitchell, et al., Determinants of Elevated Pulse Pressure in Middle-Aged and Older Subjects With Uncomplicated Systolic Hypertension, Circulation, 108(13):1592-1598 (Sep. 2003).
Mottram, et al., Relation of Arterial Stiffness To Diastolic Dysfunction In Hypertensive Heart Disease, Heart, 91(12):1551-1556 (Dec. 2005).
Nguyen et al., "Non-Invasive Monitoring of Cardiac Output in Critical Care Medicine," Front Med (Lausanne), vol. 4—pp. 1-8, (Nov. 2017).
Pak, et al., Mechanism of Acute Mechanical Benefit From VDD Pacing In Hypertrophied Heart, Circulation, 98(3):242-248 (Jul. 1998).
Reymond, et al., Validation of a One-Dimensional Model of the Systemic Arterial Tree, Am. J. Physiol. Heart Circ. Physiol., 297(1):H208-222 (Jul. 2009).
Reymond, et al., Validation of a Patient-Specific One-Dimensional Model of the Systemic Arterial Tree, Am. J. Physiol. Heart Circ Physiol., 301(3):H1173-1182 (Sep. 2011).
Safar, et al., Arterial and Venous Compliance in Sustained Essential Hypertension, Hypertension, 10(2):133-139 (Aug. 1987).
Sagawa, et al., End-Systolic Pressure/vol. Ratio: A New Index of Ventricular Contractility, The American Journal of Cardiology, 40(5):748-753 (Nov. 1977).
Sakuragi, et al., Arterial stiffness: Methods of measurement, physiologic determinants and prediction of cardiovascular outcomes, International Journal of Cardiology, 138(2):112-118 (Jan. 2010).
Segers et al., Pulse Pressure Method and the Area Method For The Estimation of Total Arterial Compliance in Dogs: Sensitivity to Wave Reflection Intensity, Annals of Biomedical Engineering, 27(4):480-485 (Aug. 1999).
Segers, et al., Three-and four-element Windkessel models: assessment of their fitting performance in a large cohort of healthy middle-aged individuals, Proceedings of the Institution of Mechanical Engineers, Part H: Journal of Engineering in Medicine, 222:417-428 (2008).
Senzaki, et al., Single-Beat Estimation of End-Systolic Pressure-Volume Relation In Humans, Circulation, 94(10):2497-2506 (Nov. 1996).
Shishido, et al., Single-Beat Estimation of End-Systolic Elastance Using Bilinearly Approximated Time-Varying Elastance Curve, Circulation, 102(16):1983-1989 (Oct. 2000).
Starling, et al., The Relationship of Various Measures of End-Systole to Left Ventricular Maximum Time-Varying Elastance in Man, Circulation, 76(1):32-43 (Jul. 1987).
Stergiopulos, et al., Use of pulse pressure method for estimating total arterial compliance in vivo, Am. J. Physiol., 276(2):H424-428 (Feb. 1999).
Suga, et al., Instantaneous Pressure-Volume Relationships and Their Ratio in the Excised, Supported Canine Left Ventricle, Circulation Research, 35(1):177-126 (Jul. 1974).
Vardoulis, et al., Validation of a novel and existing algorithms for the estimation of pulse transit time: advancing the accuracy in pulse wave velocity measurement, Am. J. Physiol. Heart Circ. Physiol., 304:H1558-1567 (Jun. 2013).

* cited by examiner

SYSTEM AND METHODS FOR REAL TIME NONINVASIVE ESTIMATION OF CARDIOVASCULAR PARAMETERS USING MACHINE LEARNING

CROSS-REFERENCE TO RELATED APPLICATIONS

This application is a national phase application under 35 U.S.C. § 371 of PCT/IB2020/057656, filed Aug. 14, 2020, which claims the benefit of priority of U.S. Provisional Patent Application No. 63/058,405, filed Jul. 29, 2020, and U.S. Provisional Patent Application Ser. No. 62/889,535, filed Aug. 20, 2019, the entire contents of each of which are incorporated herein by reference.

FIELD OF THE INVENTION

The present invention relates generally to systems and methods for estimating cardiovascular hemodynamic parameters, including cardiac output, central systolic blood pressure, left ventricular end-systolic elastance, arterial compliance and aortic impedance, using selected arterial models calibrated using patient specific noninvasively measured physiologic parameter values and optionally machine learning.

BACKGROUND OF THE INVENTION

The development of proper diagnostic and/or treatment strategies for patients with impaired cardiovascular function requires a physician to evaluate multiple cardiovascular hemodynamic parameters, such as cardiac output (CO), aortic (central) systolic blood pressure (cSBP), left ventricular end-systolic elastance (Ees), total arterial compliance (CT) and aortic impedance (Zao). For example, CO is a primary determinant of global oxygen transport from the heart to the human body. CO is generally considered a useful index for predicting clinical outcomes and effectively assessing cardiovascular disease. Critically ill or intensive care unit (ICU) patients often require continuous assessment of CO for diagnostic purposes and/or for guiding therapeutic interventions.

Previously known methods and systems for measuring CO include invasive techniques, such as the Fick method and the thermodilution method. The Fick method utilizes a pulmonary artery catheter and other special devices to measure oxygen consumption by the lungs and the arteriovenous difference in oxygen. CO is calculated by dividing the oxygen consumption of the lungs by the arteriovenous difference in oxygen. The thermodilution method uses a pulmonary artery catheter having a thermistor to measure a decrease in temperature that results from an injection of a bolus of cold fluid into the right atrium. The Stewart-Hamilton conservation of heat equation is then used to compute CO.

Other methods of measuring CO include minimally invasive methods such as pulse contour analysis and esophageal Doppler monitoring. Pulse contour analysis requires insertion of an arterial catheter, allowing a continuous pulse waveform contour analysis to be performed. Esophageal Doppler monitoring utilizes a flexible probe to measure the blood flow velocity in the descending aorta. CO is calculated as the heart rate multiplied by the stroke volume, where the stroke volume is calculated as a function of the flow velocity and the cross-sectional area of the aorta. As an alternative to esophageal Doppler monitoring, cardiac output also may be measured using noninvasive Doppler ultrasound or Magnetic Resonance Imaging (MRI).

The convenience of previously known minimally invasive methods of measuring CO is limited by high cost and the need for specialized equipment or training. In addition, several of the previously known methods require catheterization, which is frequently associated with increased morbidity and mortality in critically ill patients. Overall, previously known methods for obtaining CO suffer from practical and cost limitations, while others are better suited as trend-monitoring devices rather than for measuring absolute CO.

In contrast to previously known CO measurement systems, such as Doppler ultrasound, which is not suited for continuous monitoring, peripheral measurements such as systolic and diastolic brachial pressure may be acquired fully noninvasively using readily available and inexpensive components, such as blood pressure cuffs and accelerometers. Moreover, such conventional components may be used for easy and continuous monitoring by attending clinical and nursing staff. This ease of use has prompted substantial efforts to develop noninvasive methods for estimating central cardiovascular quantities (e.g., central systolic blood pressure). However, despite a range of studies devoted to acquiring central pressure estimates noninvasively, no methods yet are capable of precisely predicting absolute CO using peripheral measurements. Additionally, none of the previously known CO estimation techniques account for specific arterial tree properties of each patient.

Further, blood pressure measured with a cuff and sphygmomanometer applied to the brachial artery generally is accepted as an important predictor of future cardiovascular risk. Because systolic pressure varies throughout the arterial tree, however, aortic (central) systolic pressure (cSBP) is actually lower than corresponding brachial values, although the extent of this difference is highly variable between individuals. Emerging evidence suggests that cSBP may be better a predictor of future cardiovascular events than brachial pressure. Moreover, anti-hypertensive drugs may exert differential effects on brachial artery pressure and cSBP, and confound use of brachial pressure. Basing treatment decisions on cSBP, rather than brachial pressure, is expected to have important implications for the future diagnosis and management of hypertension. Therefore, there exists a need for non-invasively determining cSBP.

Similarly, the clinical need to effectively monitoring cardiac performance and thus detect possible myocardial disorders is well established. Accurate assessment of the myocardial inotropic state, independently from preload and afterload, remains a challenge. As a result, research has oriented towards deriving a reliable and easily obtainable cardiac index that has significant diagnostic value. Preferably, such an index is indicative of myocardial contractility, and insensitive to cardiac loading conditions, and thus enabling comparison between different pathophysiological states or for different individuals. End-systolic elastance (Ees), i.e., the slope of the end-systolic pressure—volume relation, is one such index. Ees is regarded as a major determinant of left ventricular (LV) systolic performance and heart interaction within the systemic vasculature as reported, for example, in K. Sagawa, H. Suga, A. A. Shoukas, and K. M. Bakalar, "End-systolic pressure/volume ratio: a new index of ventricular contractility," Am. J. Cardiol., vol. 40, no. 5, pp. 748-753, November 1977 and S. Hiroyuki and S. Kiichi, "Instantaneous Pressure-Volume Relationships and Their Ratio in the Excised, Supported Canine Left Ventricle," Circulation Research, vol. 35, no. 1, pp. 117-126, July 1974.

The clinical applicability of use of Ees is severely hindered by two factors: the need to induce in vivo acute load alterations and the intrinsically invasive nature of known methods of measuring this index. Consequently, investigators have focused attention on establishing a reliable noninvasive method to derive end-systolic elastance from simple single-beat measurements, as described in T. Shishido, K. Hayashi, K. Shigemi, T. Sato, M. Sugimachi, and K. Sunagawa, "Single-beat estimation of end-systolic elastance using bilinearly approximated time-varying elastance curve.," Circulation, vol. 102, no. 16, pp. 1983-1989, October 2000 and H. Senzaki, C. H. Chen, and D. A. Kass, "Single-Beat Estimation of End-Systolic Pressure-Volume Relation in Humans A New Method With the Potential for Noninvasive Application," Circulation, vol. 94, no. 10, pp. 2497-2506, November 1996. Accordingly, there exists a clinical need for a way of more robustly determining Ees.

Total arterial compliance (CT) is an another important vascular property with major pathophysiological relevance, as described, for example, in M. E. Safar and G. M. London, "Arterial and venous compliance in sustained essential hypertension.," Hypertension, vol. 10, no. 2, pp. 133-139, August 1987, B. A. Haluska, "Influence of arterial compliance on presence and extent of ischaemia during stress echocardiography," Heart, vol. 92, no. 1, pp. 40-43, January 2006 and B. A. Haluska, L. Jeffriess, M. Downey, S. G. Carlier, and T. H. Marwick, "Influence of Cardiovascular Risk Factors on Total Arterial Compliance," Journal of the American Society of Echocardiography, vol. 21, no. 2, pp. 123-128, February 2008.

CT reflects the capacitive ability of the arteries to dilate under internal pressure and store blood during systole without excessive pressure rise. CT is an important determinant of central blood pressure. It is indicative of systemic vascular input impedance and affects cardiac afterload and energy requirements. For example, a decrease in CT can inhibit pressure and flow wave damping and increase left ventricular load, thus influencing cardiac function, as reported in P. M. Mottram, "Relation of arterial stiffness to diastolic dysfunction in hypertensive heart disease," Heart, vol. 91, no. 12, pp. 1551-1556, December 2005 and T. G. Papaioannou, D. S. Mathioulakis, and S. G. Tsangaris, "Simulation of systolic and diastolic left ventricular dysfunction in a mock circulation: the effect of arterial compliance," Journal of Medical Engineering & Technology, vol. 27, no. 2, pp. 85-89, January 2003. Reduced arterial compliance also is associated with hypertension. Moreover, reduction of CT leads to an increase in wave speed, and reflected waves during early systole, thereby augmenting peak systolic pressure and pulse pressure. Further, coronary perfusion may be compromised due to resulting lower diastolic pressure.

Aortic input impedance (Zao) provides a measure of the vascular load faced by the ejecting left ventricle, as described in W. R. Milnor, "Arterial impedance as ventricular afterload," Circ Res, vol. 36, no. 5, pp. 565-570, May 1975. The vascular load depends in complex fashion on the size and mechanical properties of the aorta and systemic vasculature, as described in MacDonald, D. A., Blood Flow In Arteries, The Williams & Wilkins Company, Baltimore, Md. 351-388 (1974). These determinants of impedance have been shown to change with age, as reported in B. M. Learoyd and M. G. Taylor, "Alterations with Age in the Viscoelastic Properties of Human Arterial Walls," Circulation Research, vol. 18, no. 3, pp. 278-292, March 1966. In hypertensive patients, increased Zao has been shown to correlate with increased pulse pressure, and with changes in pulse wave velocity due primarily to changes in mean arterial pressure rather than vessel stiffening, as described in G. F. Mitchell et al., "Determinants of Elevated Pulse Pressure in Middle-Aged and Older Subjects With Uncomplicated Systolic Hypertension: The Role of Proximal Aortic Diameter and the Aortic Pressure-Flow Relationship," Circulation, vol. 108, no. 13, pp. 1592-1598, September 2003.

Despite the utility of the foregoing parameters, direct in vivo, noninvasive, measurement of CT and Zao is not feasible. To overcome that drawback, methods have been proposed for indirect estimation of CT, as described in Z. Liu, K. P. Brin, and F. C. Yin, "Estimation of total arterial compliance: an improved method and evaluation of current methods," American Journal of Physiology-Heart and Circulatory Physiology, vol. 251, no. 3, pp. H588-H600, September 1986, P. Segers et al., "Pulse pressure method and the area method for the estimation of total arterial compliance in dogs: sensitivity to wave reflection intensity," Ann Biomed Eng, vol. 27, no. 4, pp. 480-485, August 1999 and N. Stergiopulos, P. Segers, and N. Westerhof, "Use of pulse pressure method for estimating total arterial compliance in vivo," Am. J. Physiol., vol. 276, no. 2 Pt 2, pp. H424-428, February 1999. Most commonly, those methods require simultaneous recording of the proximal aortic pressure wave and flow or cardiac output. Still, the complexity of such methods has limited the assessment of aortic stiffness in every day clinical practice, while other surrogates of local or regional arterial stiffness have been suggested, as described in S. Mackenzie, I. B. Wilkinson, and J. R. Cockcroft, "Assessment of arterial stiffness in clinical practice," QJM, vol. 95, no. 2, pp. 67-74, February 2002 and S. Sakuragi and W. P. Abhayaratna, "Arterial stiffness: methods of measurement, physiologic determinants and prediction of cardiovascular outcomes," Int. J. Cardiol., vol. 138, no. 2, pp. 112-118, January 2010. Accordingly, there still exists a clinical need for accurate estimation of CT and Zao.

In view of the drawbacks of previously known CO estimation systems and methods, it would be desirable to provide systems and methods for obtaining CO that are fully noninvasive and easily implemented in a routine clinical setting. It further would be desirable to provide systems and methods for estimating CO and other cardiovascular parameters that reduce costs compared to previously known noninvasive and invasive techniques.

It therefore would be desirable to provide a noninvasive system and method for estimating key vascular hemodynamic parameters, such as CO, cSBP, Ees, CT and Zao, to improve patient diagnosis and treatment strategies.

SUMMARY OF THE INVENTION

Systems and methods are provided that use patient-specific noninvasive physiologic measurements to estimate cardiovascular hemodynamic parameters that are not noninvasively measurable. In accordance with one aspect of the invention, systems and methods for estimating cardiac output for a patient are provided, wherein a numerical model first is personalized for a patient using patient-specific noninvasive physiologic measurements, and then the personalized model is used to periodically or continuously estimate CO using subsequent noninvasively physiologic measurements.

For example, the method includes noninvasively obtaining for a patient a measured blood pressure value, e.g., a diastolic brachial pressure value or a systolic brachial pressure value, or both, and a measured pulse wave velocity. The patient-specific noninvasive physiologic measurement used to personalize the model may include a measured blood pressure value, obtained using a blood pressure cuff or like device, and a measured pulse wave velocity value, obtained using one or more accelerometers, pressure tonometers, or other non-invasive sensors capable of sensing pressure, flow (velocity) or arterial diameter changes during the pulse cycle. The accelerometers or like devices may be positioned at proximal and distal sites, for example, adjacent the femoral and carotid arteries of the patient, such that the measured pulse velocity value is obtained by measuring propagation time of an arterial pulse from the proximal site, e.g., in the vicinity of the carotid artery or near the heart, to the distal site, e.g., near the femoral artery or away from the heart.

In one embodiment, the numerical model includes an arterial tree model that is personalized using by first iteratively computing, while adjusting one or more other variables of the arterial tree model such as vessel distensibility, resistance or stroke volume, a blood pressure value until a difference between the measured blood pressure value and the computed blood pressure value is less than a selected first threshold. Once the difference between the computed and measured blood pressure values converges, other variables of the arterial tree model are adjusted during a further iterative process until a difference between a measured pulse wave velocity value and a computed pulse wave velocity value is less than a second threshold. When the numerical model converges on both the blood pressure value and the pulse wave velocity solution, it is fully personalized to provide patient-specific estimates for additional values of measured blood pressure and pulse wave velocity.

An exemplary system for implementing a patient-specific numerical model for noninvasively estimating cardiac output of a patient includes one or more sensors for measuring at least one of a blood pressure value or a pulse wave velocity of the patient, and non-transitory computer readable media. The non-transitory computer readable media includes instructions that, when executed by a processor, cause the processor to perform the method described above. The system further may include one or more sensors, e.g., a blood pressure cuff for measuring the blood pressure value and one or more accelerometers or like devices for measuring the pulse wave velocity value.

In accordance with a further aspect of the invention, a numerical model as described above may be employed with a synthetic dataset and machine learning to create an estimator for noninvasively predicting multiple cardiovascular parameters. To achieve this goal, an inverse problem solving method is employed first, wherein the one-dimensional cardiovascular model is adjusted to predict cardiac output (CO) and aortic (central) systolic blood pressure (cSBP), with an acceptable degree of accuracy, using selected physiologic parameters that are non-invasively measured from a representative actual patient population. Once the one-dimensional model is tuned based on representative patient data, it may be used with additional values of patient-specific noninvasively measured physiologic parameters to generate real-time estimates of CO, which is not non-invasively observable.

Next, the tuned one-dimensional cardiovascular model is run, using as inputs the noninvasively measured physiologic parameters stepped computationally through their expected physiologic ranges, to generate a synthetic dataset. Using machine learning algorithms and additional non-invasively measurable parameters, such as ECG waveform timing data and heart sound timing data, the information in the synthetic dataset is correlated to additional noninvasively unobservable physiologic parameters, such as left ventricular end-systolic elastance (Ees), total arterial compliance (CT) and aortic impedance (Zao). The output of machine learning analyses is a database that covers the physiologically useful ranges of each of the noninvasively measurable physiologic parameters and algorithms for correlating that data to the clinically relevant noninvasively unobservable cardiovascular parameters. The resulting algorithms and database then may be used in a clinical setting to generate, in real time, estimated values of CO, cSBP, Ees, CT, and Zao for patients for whom non-invasively measured physiologic parameters are available. Accordingly, the inventive system and methods enable a clinician to treat and diagnose patients afflicted with cardiovascular maladies using preferred hemodynamic indices using only readily available noninvasively measured physiologic data.

In a preferred embodiment, the foregoing system comprises a computer configured to store a database generated as described above, one or more sensors configured to noninvasively measure selected physiologic parameters and generate program inputs, and a computer programmed to receive the program inputs and apply computational routines to analyze the database to generate as outputs estimates of the preferred cardiovascular and hemodynamic outputs, such as CO, cSBP, Ees, CT, and Zao. The patient-specific noninvasive physiologic parameter measurements may include a measured blood pressure value, obtained using a blood pressure cuff, and a measured pulse wave velocity value, obtained using one or more sensors for acquiring a pulse signal at arterial sites. The pulse sensors may be configured to be positioned adjacent proximal and distal arterial sites of the patient, for example, at the carotid and femoral arteries respectively, such that the measured pulse velocity value is obtained by measuring propagation time of an arterial pulse from the carotid artery to the femoral artery. Responsive to the input patient-specific noninvasive physiologic parameter measurements, the program analyzes the database, generates and displays for health care workers, in real time, estimates for the desired, but unobserved, hemodynamic indices. Suitable sensors may include accelerometers, vibrometers, optical sensors, or tonometer or Doppler-based sensors.

Methods for creating and using the above-described database and algorithms for use in the inventive systems also are provided.

DETAILED DESCRIPTION OF THE INVENTION

Figure 1:
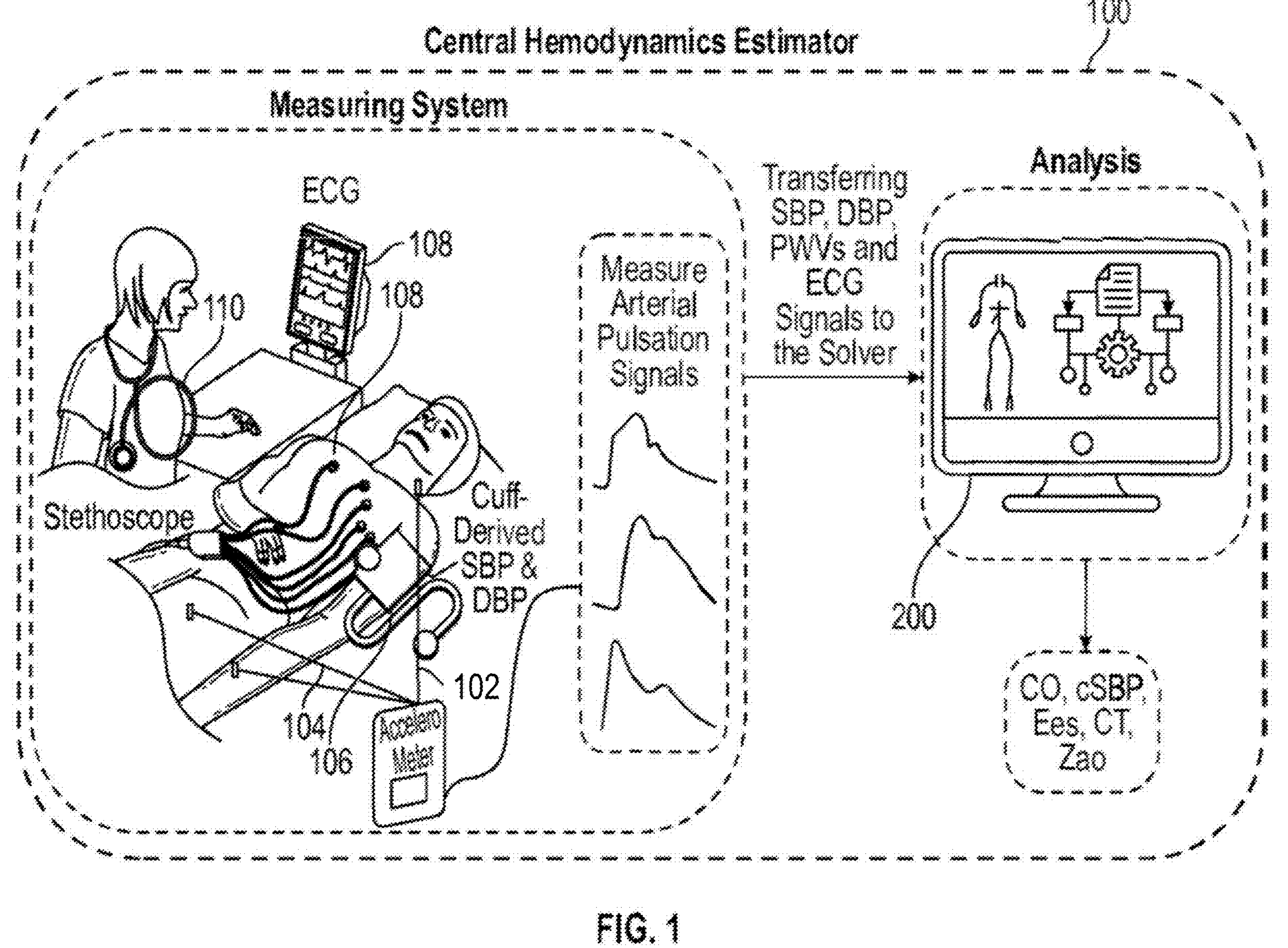
FIG. 1 illustrates an exemplary system for noninvasively estimating cardiovascular and hemodynamic parameters of a patient in accordance with the principles of the present invention.

The present invention is directed to systems and methods for providing real time estimates of selected vascular hemodynamic parameters using patient-specific values of noninvasively measured physiologic parameters.

In accordance with one aspect of the invention, a personalized numerical model of an arterial tree may be created to provide a patient-specific estimator of cardiac output for a patient based on noninvasively measured physiologic parameters. The patient-specific estimator, once calibrated, may be used continuously or intermittently to provide CO estimates using physiologic data obtained with inexpensive and readily available monitoring components, such as automatic blood pressure cuffs and pulse sensors.

More specifically, in one embodiment CO may be accurately estimated using noninvasively obtained patient-specific information, such as blood pressure and pulse wave velocity measurements, to first personalize a numerical arterial tree model, and following such calibration, may be used with subsequently obtained noninvasive measurements to provide updated CO and cSBP values. A generalized one-dimensional (1-D) arterial tree model is personalized using measurements of blood pressure, e.g., brachial systolic and diastolic blood pressure, heart rate (HR), and pulse wave velocity, e.g., carotid-to-femoral pulse wave velocity (cf-PWV) of a patient. A two-layer optimization process is employed calibrate the numerical model with the measured patient data, during which calibration process arterial model parameters are adjusted so that model predictions converge, to within a specified threshold, of the noninvasive patient data. Once the numerical model is calibrated to an initial set of patient data, the patient-specific model may thereafter be used to predict CO and CSBP for subsequent set of noninvasively measured patient physiologic values.

In accordance with a further aspect of the invention, the above systems and methods may be generalized, in which a one-dimensional cardiovascular model may be trained and calibrated using non-invasively measured and invasively measured physiologic parameter values from a representative patient population. Thereafter, additional values for the non-invasively measurable parameters are synthetically generated for clinically useful physiologic ranges and input to the model to generate additional synthetic values of the unmeasured cardiovascular parameters of interest. Machine learning algorithms then are applied to the synthetic dataset to generate algorithms that correlate the noninvasively measurable patient physiologic parameters to desired vascular hemodynamic parameters heretofore obtainable only via invasive measurements. Once the database and algorithms are created, the system and methods of the present invention may be used to generate real time estimates for key cardiovascular parameters, previously measurable only by invasive techniques, using physiologic data obtained with inexpensive and readily available monitoring components, such as automatic blood pressure cuffs, pulse sensors and conventional ECG systems.

In accordance with this further aspect of the present invention, methods are provided for accurately estimating selected cardiovascular parameters, including CO, cSBP, Ees, CT, and Zao using noninvasively obtained patient-specific information, such as blood pressure and pulse wave velocity measurements, together with a synthetic database and machine learning algorithms trained on that database. The synthetic database also is generated using the generalized one-dimensional (1-D) arterial tree model calibrated with actual measurements of blood pressure, e.g., brachial systolic and diastolic blood pressure, heart rate (HR), and pulse wave velocity, e.g., carotid-to-femoral pulse wave velocity (cf-PWV) of a patient. In an exemplary embodiment, a two-layer optimization process is employed calibrate the numerical model with the measured patient data, wherein arterial model parameters are iteratively adjusted so that model predictions converge, to within a specified threshold, of the noninvasively measure patient data. Once the numerical model is calibrated, additional values of noninvasively measurable patient physiologic parameters are input to the model to generate additional synthetic estimates to complete the dataset. Machine learning algorithms, including regression and classification are used to analyze the resulting dataset, together with noninvasively measured physiologic values, to generate a model that provides real time estimates for the non-invasively unobservable hemodynamic parameters.

In a preferred embodiment, four easily obtainable inputs are employed: noninvasive brachial systolic blood pressure (SBP); brachial diastolic blood pressure (DBP); heart rate; and pulse wave velocity (PWV). A measured set of these data may be used to adjust a one dimensional arterial tree model, such as that described in P. Reymond et al. "Validation of a patient specific one-dimensional model of the systemic arterial tree," Am. J. Physiol. Heart Circ. Physiol., 301(3):H1173-1182 (September 2011), to accurately predict mean flow (i.e., cardiac output) at the aortic root.

Training and calibration of a generic arterial tree model with clinically relevant noninvasive data is expected to enable generation of clinically accurate absolute values of CO and trends without the cost and complexity of previously-known used CO measurement techniques. PWV is routinely measured in clinical practice and has been identified as an independent predictor of cardiovascular disease, especially when it used in conjunction with pressure measurements. Low cost, readily available sensors, such as a blood pressure cuff and pulse sensors, may be employed to obtain noninvasive physiologic measurements, thereby providing a reduced-cost system, compared to previously known systems such as, e.g., esophageal Doppler, partial carbon dioxide rebreathing, and volume clamping. Additional vascular hemodynamic parameters may be derived from those non-invasive physiologic parameters values, as described herein, thus enabling real time prediction for clinical application of CO and other key cardiovascular parameters.

Referring now to FIG. 1, exemplary system 100 is described for noninvasively estimating CO of a patient, and optionally, additional parameters including cSBP, Ees, CT and Zao. System 100 includes one or more sensors, e.g., pulse sensors 102 and 104, blood pressure cuff 106, optional ECG system 108 and heart sound detector 110, e.g., a stethoscope, and console 200. Console 200 receives the output from sensors 102, 104, cuff 106, and optionally, ECG system 108 and from a clinician who inputs certain data determined using stethoscope 110. Console 200 is programmed with software that analyzes the input data and executes the inventive estimator algorithms. The one or more sensors are operatively coupled to console 200 via cables or alternatively, via wireless transmission.

In one preferred embodiment, pulse sensor 102 is an accelerometer configured to be located on the patient's skin in the vicinity of a carotid artery, while pulse sensor 104 is an accelerometer configured to be located in the vicinity of a femoral artery. Each of pulse sensors 102 and 104 may be disposed on a patch that includes a biocompatible adhesive for securing the patch to the patient's skin in. Blood flow pulse detected by pulse sensors 102 and 104 during the cardiac cycle are transmitted to console 200, where that information is used to determine the time for an arterial pulse to propagate from the carotid to the femoral artery, referred to herein as the "carotid to femoral pressure wave velocity" or "cf-PWV". Pulse sensors 102 and 104 may be connected to console 200 via electrical leads, or alternatively may be coupled to a transmitter that sends the measured outputs of the accelerometers to console 200 wirelessly, e.g., via transmitters that comply with Bluetooth® or IEEE® 802.11 standards. In alternative embodiments, pulse sensors 102 and 104 may comprise vibrometers, optical sensors, or tonometer or Doppler-based sensors.

Blood pressure cuff 106 may comprise an automated blood pressure cuff configured to be disposed on a patient's arm, e.g., a commercial oscillometric cuff, and measures brachial systolic blood pressure (SBP) and brachial diastolic blood pressure (DBP). Data output by cuff 106 are transmitted to console 200 for processing via electrical leads or wirelessly. As will be understood, cuff 106 does not provide continuous pressure readings, but only at periodic intervals set using the cuff controller (not shown) or console 200.

As further discussed below, for prediction of certain cardiovascular parameters, the output of heart sound detector 110 and ECG system 108 may be required. Heart sound detector 110 may be a conventional acoustic or electronic stethoscope, by which a clinician determines certain heart sounds corresponding to cardiac valve events, as described below, the occurrence of which the clinician inputs to console 200 via an input device. Alternatively, as will be understood by one of skill in the art, an automated system may be employed for electronically detecting heart, the output of which is provided directly to console 200 without clinician intervention. ECG system 108 may be a conventional ECG multi-lead system, preferably 5 to 12 leads, and generates an electrocardiograph waveform that is input to console 200.

Console 200 may be programmed to output values of estimated real time cardiovascular parameters to a video display or to graphical plotter, to transmit such estimated values to a central monitoring system or nursing station, to generate a report, and/or to monitor trends in estimated values and to generate alarms or notifications if one or more estimated values falls below clinically acceptable levels.

Figure 2:
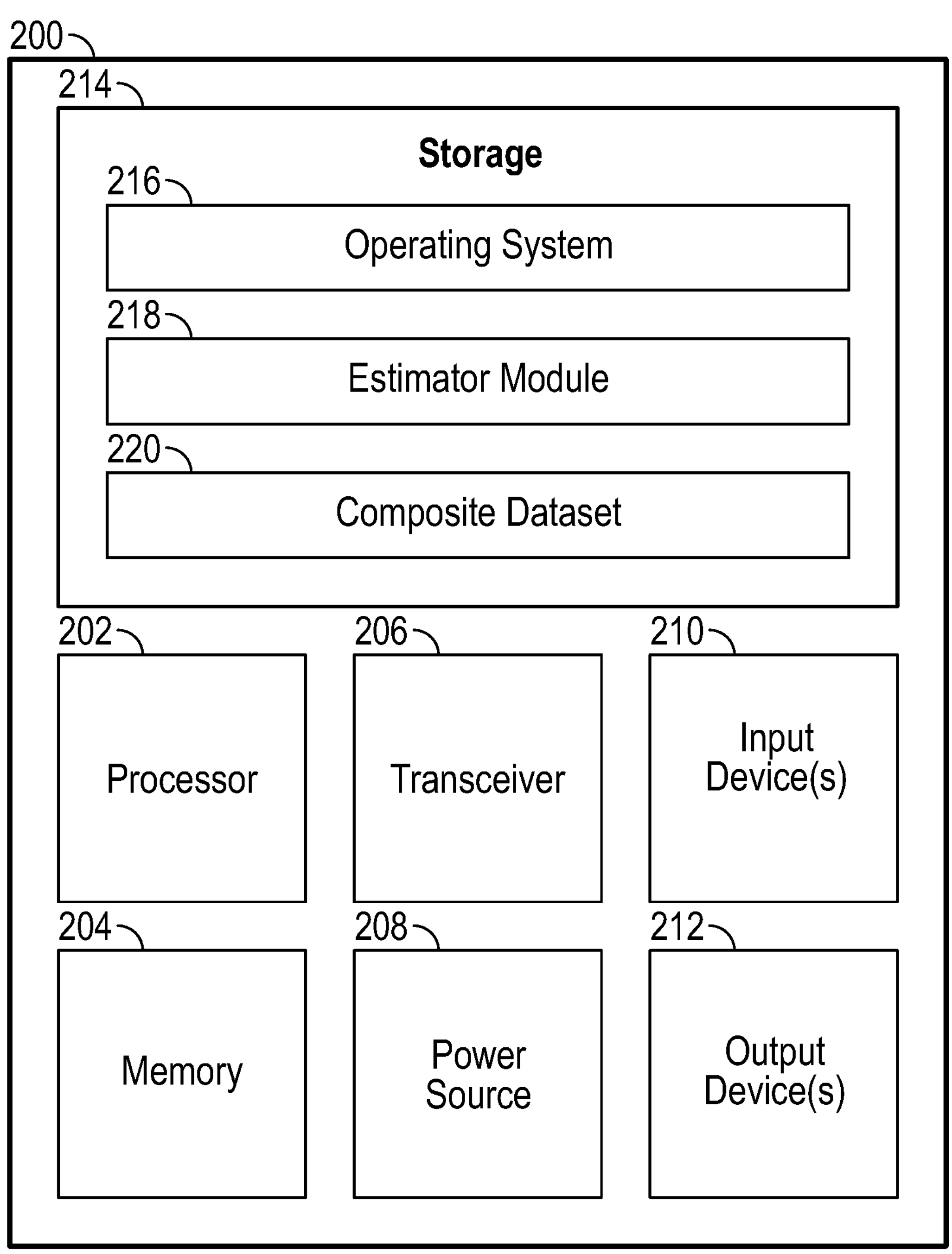
FIG. 2 is a schematic view of exemplary hardware and software components of a console of the present invention.

Exemplary hardware and software components of console 200 are now described with respect to FIG. 2. Console 200 includes a computer, e.g., laptop, desktop, or tablet that is programmed with the inventive estimator software as described herein, and includes at least one processor 202, memory 204, non-volatile storage 214, transceiver 206, power source 208, and one or more input devices 210 and output devices 212.

Processor 202 may be a conventional multi-core processor, such as an Intel® CORE™ i5 or i7 processor. Memory 204 may comprises volatile (e.g. random-access memory (RAM)), non-volatile (e.g. read-only memory (ROM)), flash memory, or any combination thereof. Transceiver 206 may receive and/or transmit information to and from other components in system 100 including pulse sensors 102 and 104, cuff 106, and optional heart sound detector 108 and ECG system 110, using any well-known communication infrastructure facilitating communication over wired or wireless connection, such as any IEEE® 802 standard. Power source 208 preferably connects to a standard wall outlet and/or may include a battery. Non-volatile storage 214 preferably includes removable and/or non-removable storage, such as, solid-state disk memory of magnetic hard drive.

Input device 210 may be one or more devices coupled to, or integrated into, console 200 for inputting data to the console, and may include, for example, a keyboard or touchscreen, a mouse and/or a pen. Input device 210 may be used to input patient specific information into the estimator, e.g., height, age, weight, gender, and identity, and/or to modify the sampling rate of pulse sensors 102 and 104, the frequency with which pressure measurements are taken with cuff 106, or the sampling of the outputs of ECG system 108 or heart sound detector 110. Output device 212 may be any suitable device coupled to or integrated into console 200 for outputting or otherwise displaying data, such as video screen, printer or plotter. Output device 212, further may include a speaker or alarm bell that may be activated if one or more of the monitored estimated parameter values falls below a clinically significant threshold indicating patient distress.

Still referring to FIG. 2, operating system 216 and estimator module 218 are stored in non-volatile storage 214. Operating system 216 includes the operating system for console, e.g., Microsoft® Windows® or Linux®, as well as the necessary drivers for the input and output devices. Estimator module 218 may be personalized for a specific patient, or in an alternative embodiment may include machine learning and search algorithms for analyzing the input patient-specific values and optional composite dataset or database 220 to generate real-time values for CO, cSBP, Ees, CT and Zao. Estimator module 218 also may include programming for communicating with and adjusting the input sampling rates for inputs received from pulse sensors 102 and 104, cuff 106, ECG system 108 and heart sound detector 110, and further for generating output to be displayed on output device 212.

Estimator module 218 includes programmed instructions that enable generation of a patient-specific estimator by personalizing a generic arterial tree model using noninvasively physiologic patient data measurements. Specifically, the estimator module may employ a two-layer optimization algorithm for personalizing a generic 1-D arterial tree model using noninvasively-measured patient physiologic data, which thereafter may be used to estimate CO and other parameters for a range of measured data values for that specific patient.

Figure 3:
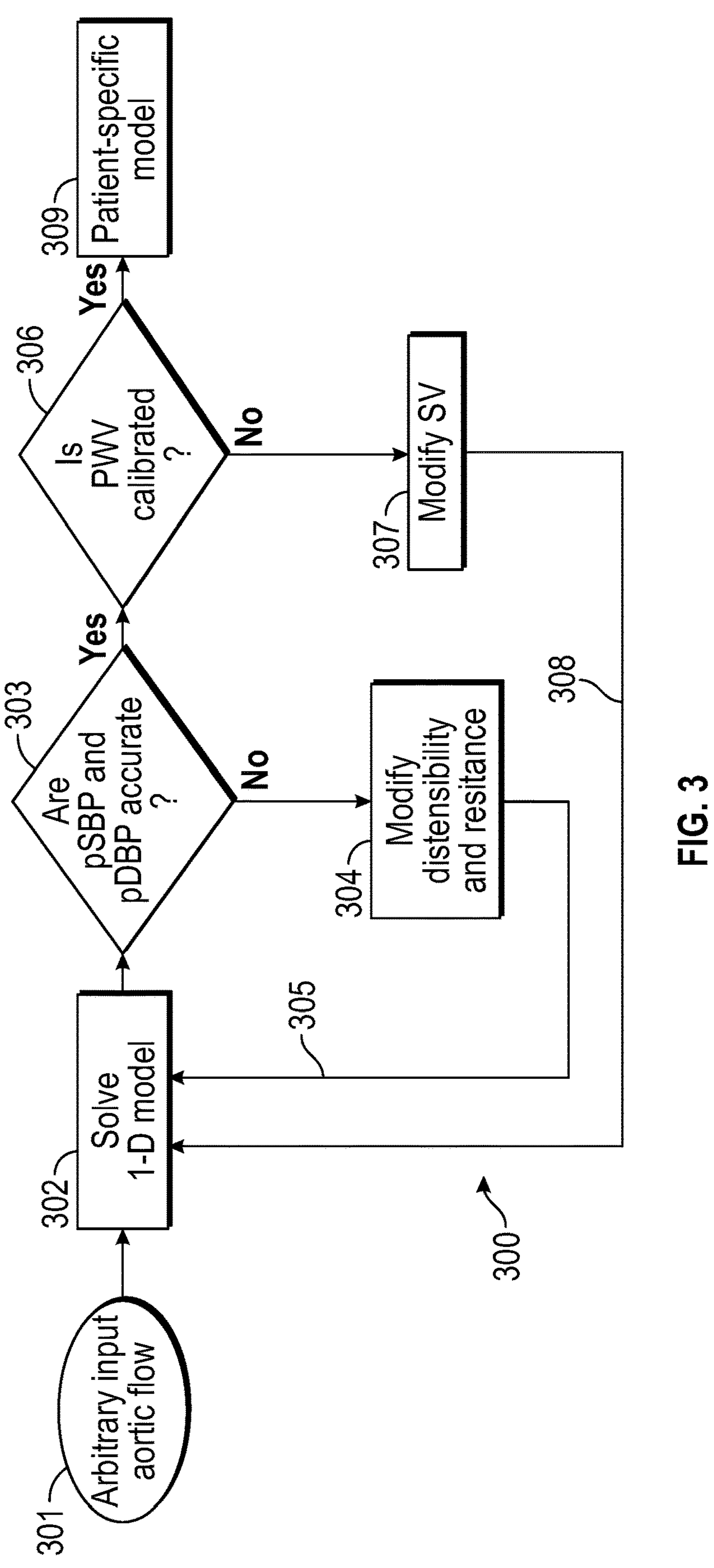
FIG. 3 is a flowchart of an exemplary inverse problem-solving model having two layers of optimization for estimating vascular parameters using noninvasive measurements in accordance with the principles of the present invention.

Referring to FIG. 3, an exemplary, generic one dimensional arterial tree model, such as that described in P. Reymond, et al., "Validation of a one-dimensional model of the systemic arterial tree," Am. J. Physiol. Heart Circ. Physiol., 297(1):H208-222 (July 2009), is trained and calibrated with data from a single patient to generate a patient-specific estimator. Alternatively, the estimator may be trained on patient data for a representative patient population, and the model then used to generate synthetic data that is analyzed with machine learning algorithms. That arterial tree model describes the fluid dynamic characteristics of the main arteries of systemic circulation, and includes a detailed representation of the cerebral circulation and the coronary circulation networks. The governing equations of the model are obtained by integration of longitudinal momentum and continuity of the Navier-Stokes equations over the arterial cross sections.

Propagations of pressure and flow waves throughout the vasculature are obtained by solving the governing equations using an implicit finite-difference scheme, in which the arterial segments are modeled as long tapered tubes having compliances defined by a nonlinear function of pressure and location. In the model, arterial wall behavior is considered nonlinear and viscoelastic, and local arterial compliance is calculated after approximating pulse wave velocity (PWV) as an inverse power function of arterial lumen diameter, using the measured physiologic values. Distal vessels of the model are terminated with three-element Windkessel models, and resistance of the peripheral vasculature is accounted for by coupling distant vessels with three-element Windkessel models. As input, the arterial tree receives either a prescribed input aortic flow waveform or is coupled with a time-varying elastance model to simulate contractility of the left ventricle.

For a given set of values of peripheral SBP and DBP, HR, and cf-PWV, solving the arterial tree model generates a single corresponding value of CO and cSBP, assuming other model parameters are constrained within the range of physiologically possible values. Thus, by simultaneously adjusting such properties/variables of the model and specifying input aortic blood flow to capture a given peripheral (brachial) pressure and cf-PWV, an estimator may be generated that is specifically calibrated for an individual patient. Once that initial calibration of the estimator is completed, the estimator may be used to generate additional values of CO over a range of clinically useful values of the measured physiologic values for that specific patient. Alternatively, in accordance with another aspect of the present invention, the estimator may be trained and calibrated over measure data from a representative patient population. In this case, machine learning may be employed to correlate datasets output by the model with additional non-invasively measurable patient physiologic data to derive estimated values for other cardiovascular parameters, including Ees, CT and Zao.

The inter-subject variability of arterial trees with respect to arterial compliance, total peripheral resistance, and geometry requires fine-tuning of the generic 1-D arterial model. For example, distensibility of each arterial segment may be modified in a uniform way for young individuals whereas, for older or hypertensive subjects, distensibility may be modeled as non-uniform, with more pronounced stiffening in the proximal aortic path. Data for age-related local non-uniform aortic stiffening and its effects on central circulatory hemodynamics and wave reflections are available from the scientific literature, and such data preferably are used in the arterial model to provide physiologic constraints on potential parameter ranges. Similarly, resistance may be altered in a uniform way for all terminal vessels in the model, and the geometry of the arterial vessels, i.e., diameter and length, may be assumed to be unchanged for the different individuals. Depending upon the specific implementation, such parameters may be adjusted within physiologic ranges in an iterative process to obtain a CO and cSBP solution consistent with the input measured patient values.

Still referring to FIG. 3, exemplary two-layer optimization algorithm 300 is described for calibrating the generic arterial tree model to provide a patient-specific CO and cSBP estimator. As noted above, potential ranges for physiologic parameters are adjusted while iteratively to solve the model with measured patient-specific physiologic data. To initialize the model with appropriate ranges, for example, for distensibility and resistance of peripheral vessels, the clinician may input, using input devices 210, certain static patient data, such as gender, age, body mass index or weight, and/or whether the patient has any known illnesses that affect cardiovascular health, such as diabetes, hypertension or atherosclerosis. In one embodiment, the estimator may include empirically derived equations that use such static input data to compute an initial aortic flow, indicated at 301 in FIG. 3. Alternatively, an arbitrary value of initial aortic flow may be used, which obviates the need for static input data but may require additional iterations to reach convergence.

In a first optimization loop, diastolic and systolic blood pressure values are computed using the initial aortic flow value 301 using the arterial tree model at block 302, and the computed values are compared to the values of DBP and SBP measured using cuff 106 at decision block 303. If the difference between the computed and measured values exceed a first predetermined threshold value, the distensibility and resistance characteristics of the arterial tree model are adjusted at block 304, and new values for DBP and SBP are computed along pathway 305 and block 302 until the difference between computed and measured values of DBP and SBP are less than the first predetermined threshold. Once the difference is less than the first threshold value, the first optimization loop is adjudged to have converged.

Once the computed values of DBP and SBP are judged to converge at block 303, a computed cf-PWV value is calculated analytically based on the compliance of each arterial segment in the carotid-femoral pathway. The Estimator then compares the computed cf-PWV value, at decision block 306, to the value of the carotid to femoral pressure wave determined by processing the outputs transmitted to console 200 by pulse sensors 102 and 104. If the difference between computed cf-PWV and the measured cf-PWV exceeds a second predetermined threshold, the stroke volume, i.e., the volume of blood ejected from each ventricle due to contraction of the ventricles, is adjusted at block 307 and the arterial tree model is again solved along path 308. At step 302, arterial model 302 again recalculates all pressures and flows throughout the arterial tree by repeating the first optimization loop, along path 305, to confirm that the difference between the computed to values of SBP and DBP are less than the first predetermined threshold from the measured values. Next, the computed value of cf-PWV is computed to the measured value generated from the outputs of pulse sensors 102 and 104, and the process repeats with further adjustment to the stroke volume at block 307, until the difference between the computed and measured values of cf-PWV are less than the second predetermined threshold. Once that difference is less than the second predetermined threshold, the second optimization loop is adjudged to be converged, thereby establishing a patient-specific estimator, block 309. Patient-specific estimates of the stroke volume and cSBP are provided by the patient-specific estimator. The estimated CO is determined by multiplying the stroke volume by the patient's measured heart rate (HR), as may be provided by cuff 106.

In a preferred embodiment, the first and second optimization loops may use a gradient descent approach for scaling the values of vascular compliance and resistance of the generic arterial tree model at block 304 and for adjusting the stroke volume at block 307. For example, scaling factors may be chosen so that a range of 0.1 to 3.8 mL/mmHg and 0.4 to 0.2 mmHg s/mL is covered for compliance and resistance, respectively. These limits are chosen so that the pressure values generated by the arterial tree model correspond to physiologically acceptable hemodynamic conditions. The SV scaling factors may be chosen so as the corresponding cardiac output is within the physiological range of 2 to 8 L/min. Different gradient algorithms may be used for the first and second optimization loops. And as will be understood by those familiar with finite-difference programming, alternative approaches also may be used to scale parameters, including non-gradient approaches, so long as the resulting adjustments remain within the range of physiologically acceptable hemodynamic conditions.

The two optimization loops run continuously until convergence is attained for both computed brachial SBP and DBP and computed cf-PWV. The first and second predetermined thresholds may tolerate different degrees of error, for example, the threshold for converging on brachial SBP and DBP values may be set to 0.001%, while the threshold for converging on cf-PWV may be set to 0.01%. The estimator also may include a maximum number of iterations for each optimization loop, e.g., 25, which maximum number of iterations may be different for the first and second optimization loops. If convergence on the measured parameters is not obtained when the maximum number of iterations is reached, a new value of aortic flow input may be selected at block 301, and the entire process repeated. Once the convergence is achieved for both optimization loops, the values of the distensibility and resistance are stored in memory 204, and used as the initial values for computing subsequent values of CO and cSBP responsive to changes in further measured values of DBP, SBP, cf-PWV and HR. At this point, the converged estimator may be used as a patient-specific CO and cSBP estimator for measured values of the non-invasively measured parameters.

In one embodiment, console 200 may be programmed to output patient-specific values of estimated CO and estimated cSBP to a video display or to graphical plotter, to transmit such estimated values of CO and cSBP to a central monitoring system or nursing station, to generate a report, and/or to monitor trends in estimated CO and estimated cSBP and to generate alarms or notifications if the estimated CO and estimated cSBP falls below clinically acceptable levels.

Figure 4A:
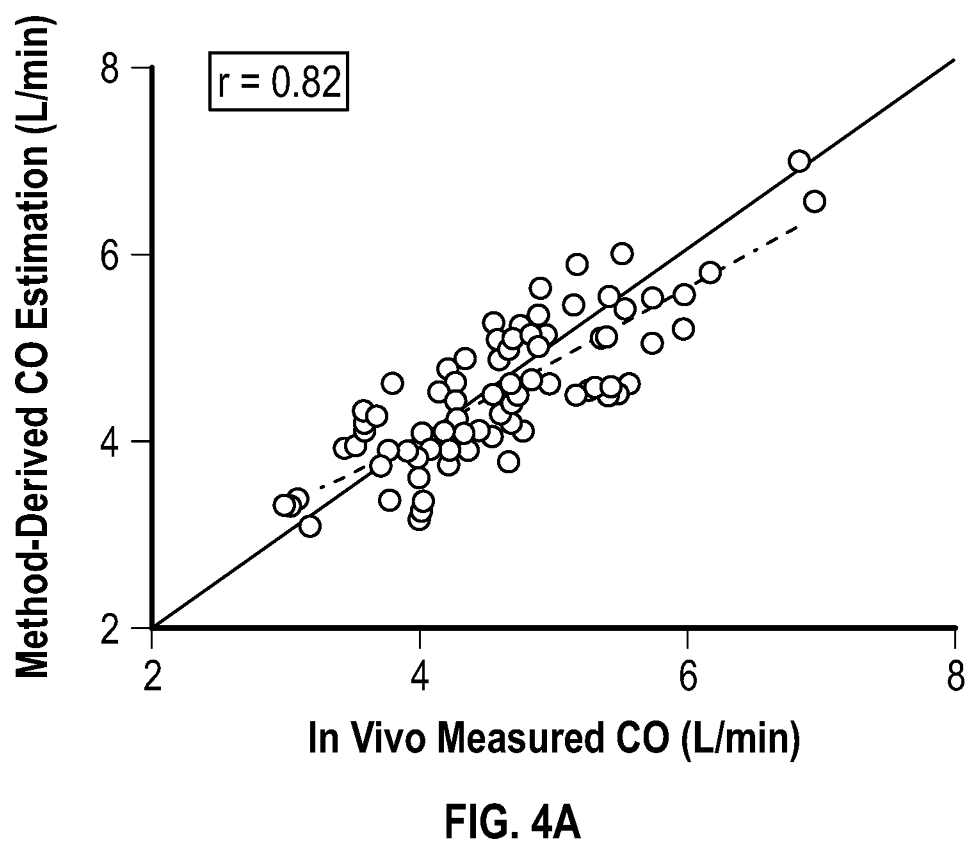
FIGS. 4A and 4B are graphs comparing results for CO predicted by an exemplary estimator of the present invention computed using noninvasive measurements against reference values of CO.
Figure 4B:
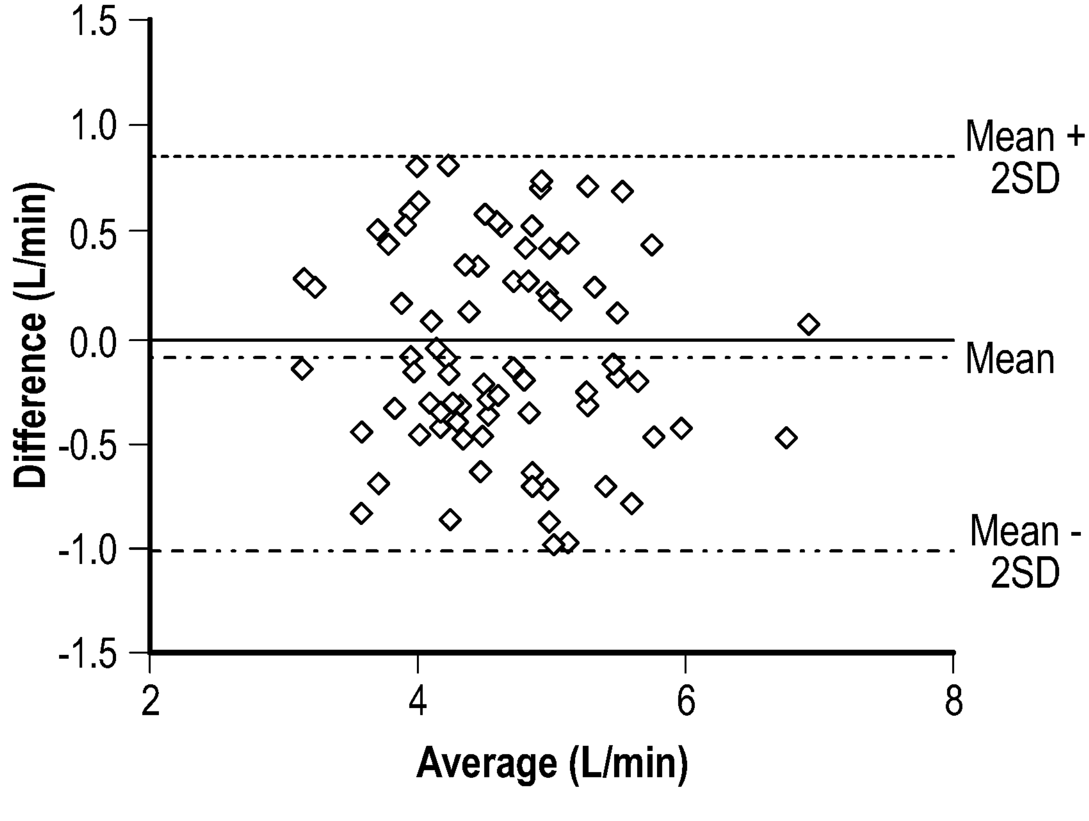

FIGS. 4A and 4B are graphs showing the results achieved by the estimator of the present invention compared to previously known CO measurements obtained with a standard reference method, two-dimensional (2-D) echocardiography, for a population of 80 adults. The study population included subjects with risk factors including, e.g., smoking, diabetes, hypertension, dyslipidemia, renal disease, cardiovascular disease, stroke, or those receiving medication.

In particular, FIG. 4A is a scatter-plot of computed CO estimates compared to in vivo measurements using the reference method, wherein the solid and dashed lines, respectively, represent equality and linear regression. FIG. 4B is the corresponding Bland-Altman plot for the same data presented in FIG. 4A, and indicates that most of CO estimates fall within +/− two standard deviations. Limits of agreement are defined by the two horizontal dotted lines.

The root mean square error (RMSE) for the estimated CO was about 0.48 L/min. In 70% of the cases, the difference between estimated CO and measured (reference) CO was below 0.5 L/min, and for 48% of the cases, the difference was below 0.35 L/min A low bias of −0.09 L/min was observed and variability of difference was found to be ±0.47 L/min, p<0.0001. Parameters of accuracy, correlation, and agreement of CO estimation by the method in comparison to the reference method are summarized in the Table 1 below.

TABLE 1

| Parameter | Value |
|---|---|
| Mean difference (L/min) | −0.09 |
| Standard deviation of difference (L/min) | 0.47 |
| Limits of Agreement (L/min) | [−1.02, 0.83] |
| Normalized root mean square error (%) | 12.01 |
| Pearson's correlation coefficient | 0.82 |
| Interclass correlation coefficient | 0.81 |

As discussed above, the foregoing 1-dimensional model also may be used to determine cSBP. More specifically, central systolic pressure (cSBP) may be derived for the cardiovascular model discussed above when tuned to patient-specific standards. Successful tuning of the generic one-dimensional tree using brachial systolic blood pressure (brSBP), diastolic blood pressure (brDBP), heart rate (HR), and carotid-to-femoral pulse wave velocity (cfPWV) provides patient specific cardiac output (CO) and cSBP. Results of the preclinical evaluation of the cSBP estimation compared to reference values of cSBP determined by previously known methods are provided in FIGS. 5A and 5B.

Figure 5A:
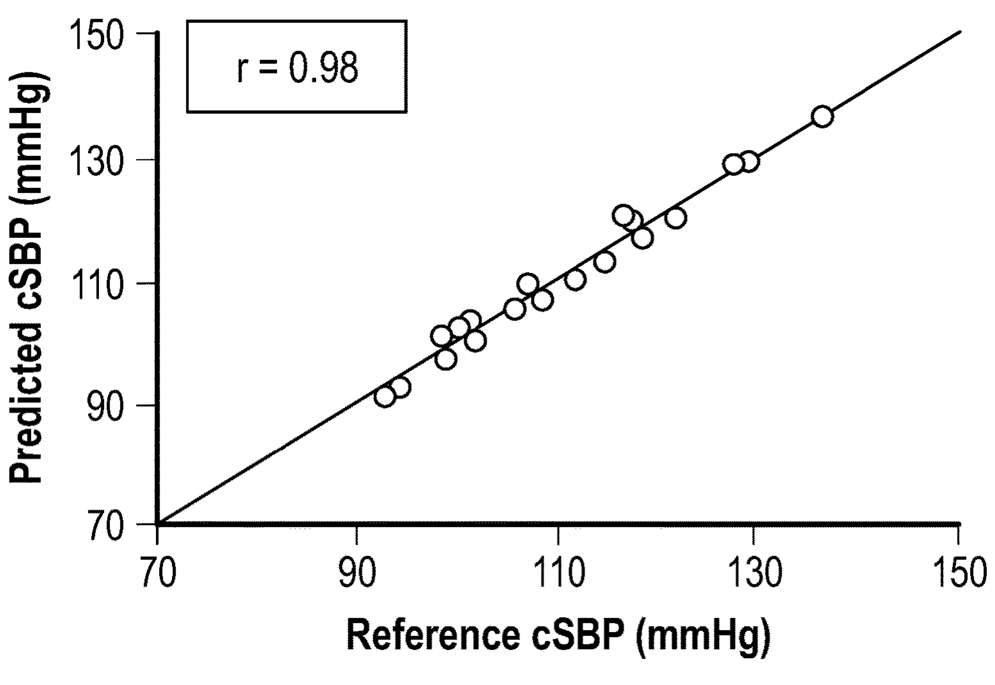
FIGS. 5A and 5B are graphs comparing results for cSBP predicted by an exemplary estimator of the present invention computed using noninvasive measurements against reference values of cSBP.
Figure 5B:
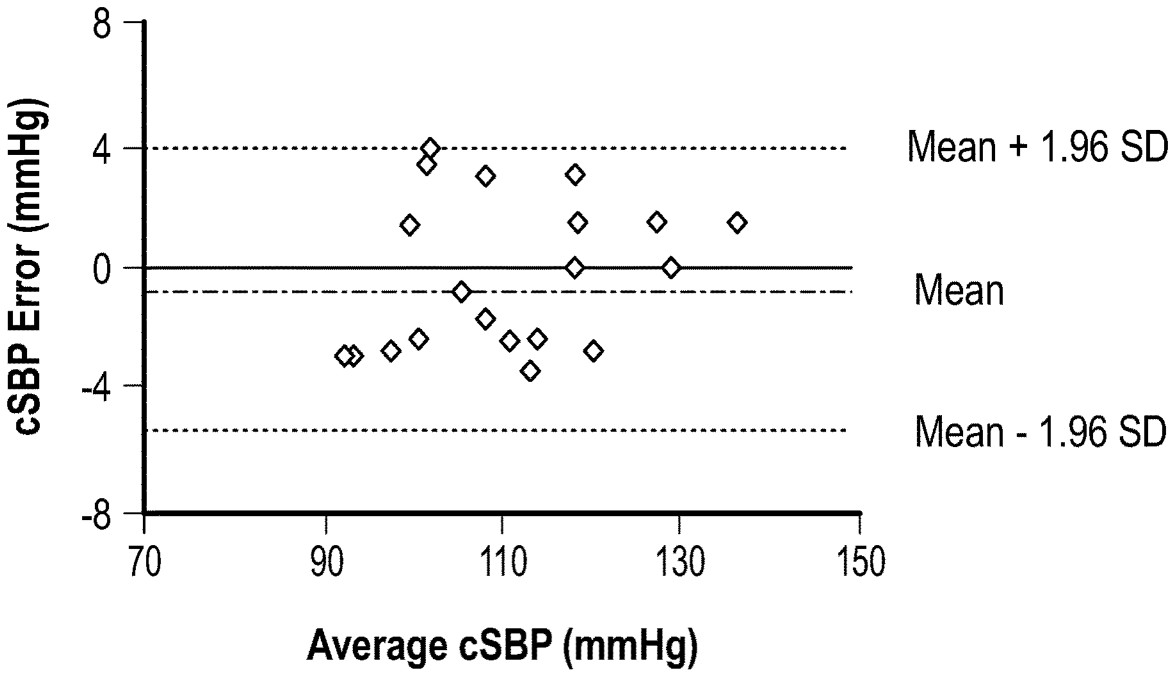

FIG. 5A is a scatterplot showing correspondence between noninvasive cSBP predictions determined using a tuned 1-Dimensional model versus in vivo measurements. The model yielded an accurate estimation of cSBP, with a root-mean-square error of 2.46 mm Hg and a Pearson's correlation coefficient of 0.98. FIG. 5B is depicts the Bland-Altman analysis, showing good agreement between the model and the reference cSBP values. In particular, the difference between estimated-cSBP and reference cSBP was less than 1.5 mmHg in 30% of the cases, ranged between 1.5 and 3.5 mm Hg for 60% of the cases, and exceeded the 3.5 mm Hg for only 10% of cases. Parameters of precision, correlation and agreement between the estimates and the actual values are shown in Table 2.

TABLE 2

| Parameter | Value |
|---|---|
| Mean difference (mmHg) | −0.27 |
| Standard deviation of difference (mmHg) | 2.51 |
| Root mean square error (mmHg) | 2.46 |
| Pearson's correlation coefficient | 0.98 |

Further in accordance with the principles of the invention, methods of providing estimates ventricular end-systolic elastance (Ees), arterial compliance (CT) and aortic impedance (Zao) are provided. This aspect of the invention does not make use of the inverse problem-solving approach discussed above, but instead relies on the machine learning models. In particular, Ees, CT, and Zao may be derived from noninvasive clinical measurements that are readily available in clinical practice using regression analysis, based on a training/testing scheme using synthetic data generated from the tuned cardiovascular model discussed above.

Using reported values of key hemodynamic values available in the literature, synthetically generated datasets were created for a generalized study population. Synthetic datasets provide a reliable and cost-effective way to correct for gaps in reference data and provide a well-balanced dataset. In one embodiment, a database of 6000 synthetic hemodynamics cases was created. In one embodiment, the 1-Dimensional cardiovascular model was run using an arbitrary but physiological set of input model parameters. Thus, instead of input data for the model coming from a patient, the model is run with an arbitrary, but clinically relevant, parameter set. For one embodiment, the input parameters of the 1-D cardiovascular model were altered by multiplying input values with different scaling factors.

For example, end-systolic and end-diastolic elastance varied in the range of 1.00-3.50 and 0.05-0.20 mmHg/mL, respectively, based on reported values for these parameters as reported, for example, in C. H. Chen, M. Nakayama, E. Nevo, B. J. Fetics, W. L. Maughan, and D. A. Kass, "Coupled systolic-ventricular and vascular stiffening with age," Journal of the American College of Cardiology, vol. 32, no. 5, pp. 1221-1227, November 1998, M. D. Feldman et al., "Acute Cardiovascular Effects of OPC-18790 in Patients With Congestive Heart Failure: Time- and Dose-Dependence Analysis Based on Pressure-Volume Relations," Circulation, vol. 93, no. 3, pp. 474-483, February 1996 and P. H. Pak, W. L. Maughan, K. L. Baughman, R. S. Kieval, and D. A. Kass, "Mechanism of Acute Mechanical Benefit From VDD Pacing in Hypertrophied Heart: Similarity of Responses in Hypertrophic Cardiomyopathy and Hypertensive Heart Disease," Circulation, vol. 98, no. 3, pp. 242-248, July 1998.

In addition, filling pressures in a range of 7.00-23.00 mmHg were used, as reported in C. H. Chen et al., "Non-invasive single-beat determination of left ventricular end-systolic elastance in humans," J. Am. Coll. Cardiol., vol. 38, no. 7, pp. 2028-2034, December 2001. The dead volume ($V_d$) and the time of maximal elastance were kept unchanged and equal to the average values of $V_d$=15.00 mL and $t_{max}$=340.00 ms, as reported in P. Reymond, F. Merenda, F. Perren, D. Rüfenacht, and N. Stergiopulos, "Validation of a one-dimensional model of the systemic arterial tree," Am. J. Physiol. Heart Circ. Physiol., vol. 297, no. 1, pp. H208-222, July 2009 and M. R. Starling, R. A. Walsh, L. J. Dell'Italia, G. B. Mancini, J. C. Lasher, and J. L. Lancaster, "The relationship of various measures of end-systole to left ventricular maximum time-varying elastance in man.," Circulation, vol. 76, no. 1, pp. 32-43, July 1987. The value of heart rate (HR) was varied between 60 and 100 bpm.

Arterial geometry was varied by adapting the height of the arterial tree, while the diameter of each arterial segment was modified uniformly to simulate different body types. The heights covered a range of 150 to 200 cm, while limits for aortic diameter of 1.90 to 4.00 cm were employed. Total peripheral resistance varied from 0.50 to 2.00 mm Hg.s/mL Total arterial compliance was chosen so that a range of 0.10 to 3.80 mL/mmHg was covered. The foregoing values correspond to an extensive range of arterial tree stiffness values, as reported in G. J. Langewouters, Visco-elasticity of the Human Aorta in Vitro in Relation to Pressure and Age. 1982 and P. Segers et al., "Three- and four-element Windkessel models: assessment of their fitting performance in a large cohort of healthy middle-aged individuals," Proceedings of the Institution of Mechanical Engineers, Part H: Journal of Engineering in Medicine.

Synthetic values for noninvasively measurable parameters, such brachial systolic blood pressure (brSBP), brachial diastolic blood pressure (brDBP) and heart rate (HR) data were generated as inputs. brSBP and brDBP correspond to pressures measured at the left brachial artery using a conventional blood pressure cuff.

The carotid to femoral pressure wave velocity (CfPWV) was derived using the tangential method described in O. Vardoulis, T. G. Papaioannou, and N. Stergiopulos, "Validation of a novel and existing algorithms for the estimation of pulse transit time: advancing the accuracy in pulse wave velocity measurement," American Journal of Physiology-Heart and Circulatory Physiology, vol. 304, no. 11, pp. H1558—H1567, June 2013. That method uses the intersection point of two tangents on the arterial pressure wave as a characteristic marker. The first tangent is defined as the line that passes tangentially through the initial systolic upstroke, i.e., the maximum of the first derivative. The second tangent line is the horizontal line passing through the minimum pressure point.

In the context of the analysis performed to generate the synthetic dataset, the method was applied to estimate the pulse transit time (PTT) between the synthetic "measured" carotid artery pressure and the synthetic "measured" femoral artery pressure, and between the synthetic "measured" carotid artery pressure and the synthetic "measured" radial artery pressure. Total aortic length was determined by summing the lengths of the arterial segments within the transmission paths. Consequently, the values of cfPWV and crPWV were calculated by dividing the respective total length by the respective PTT. In clinical practice, the same method is used to estimate cfPWV and crPWV, however, with the total arterial length of the transmission paths being approximated as, e.g., 80% of the measured distance between the two arterial sites.

Figure 6A:
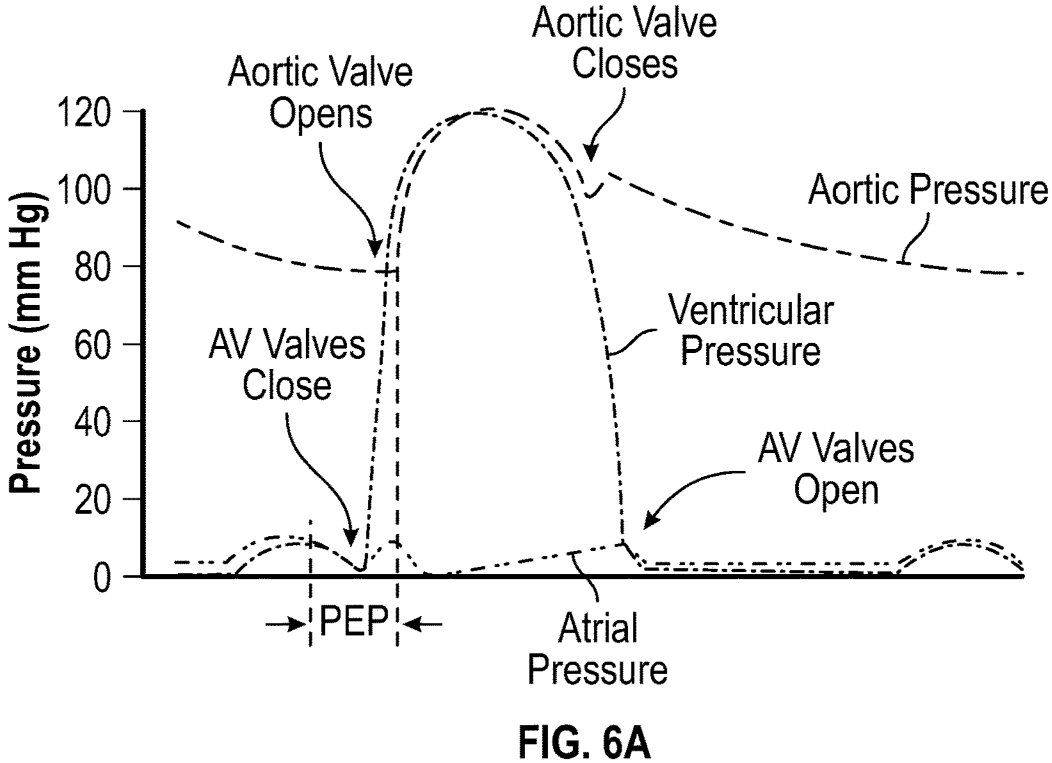
FIGS. 6A, 6B and 6C are, respectively, a graph depicting aortic blood pressure, ventricular blood pressure and atrial blood pressure fluctuations as a function of cardiac valvular events, a graph illustrating variation of left ventricular elastance as a function of time and the corresponding cardiac events, and a graph depicting the derivation of the time period between the beginning of a patient's Q-wave and closure of the aortic valve.
Figure 6B:
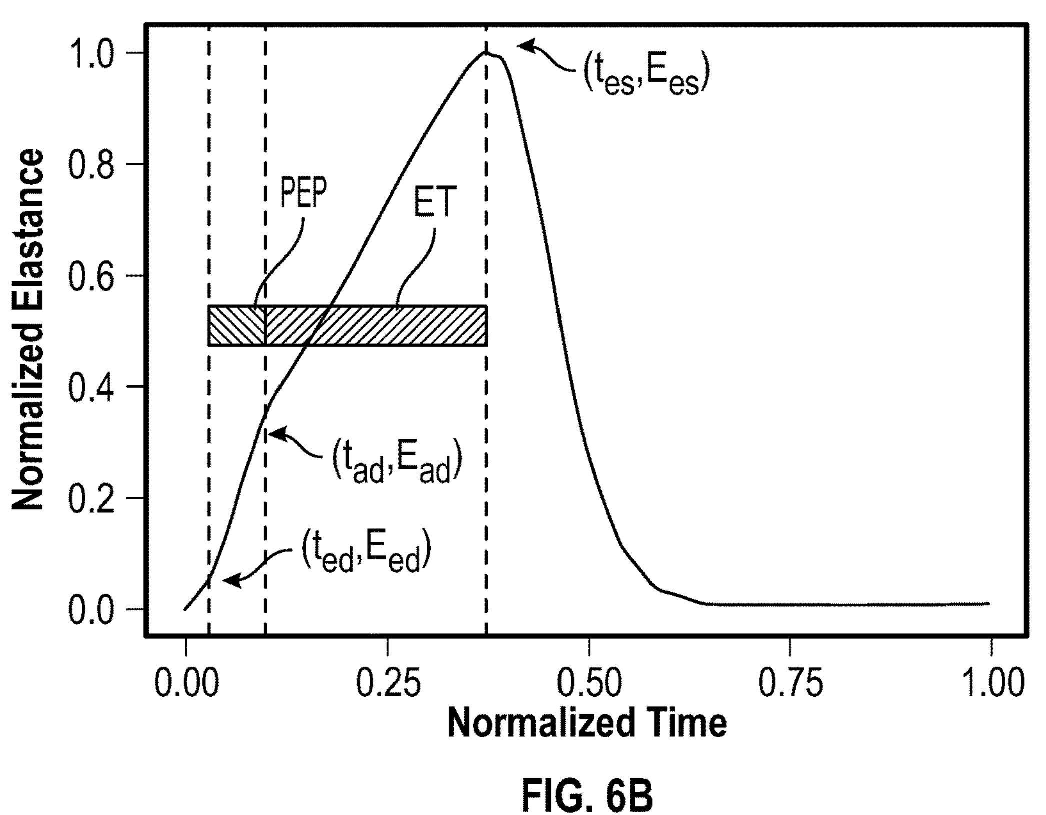
Figure 6C:
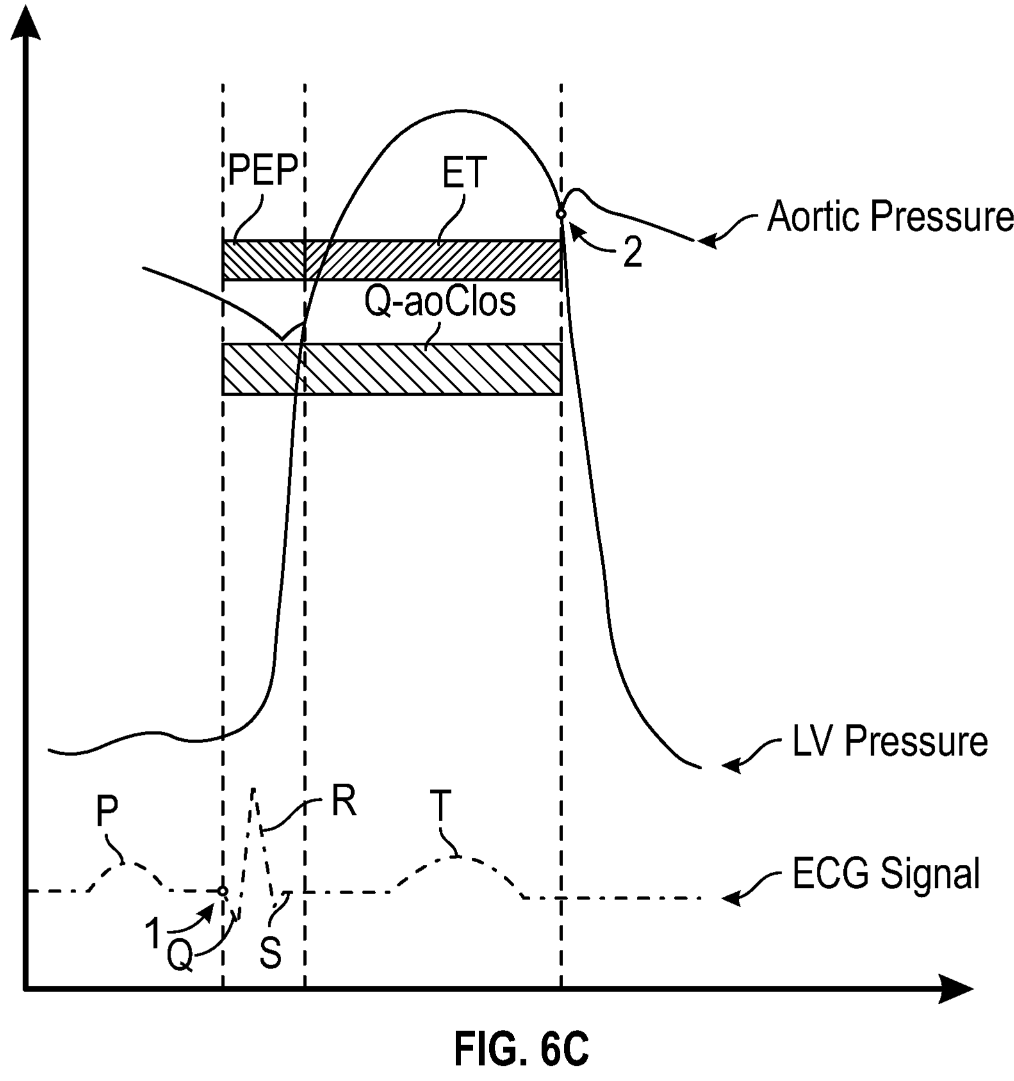

In addition, the time of the aortic valve closure was derived as the dicrotic notch point of the aortic blood pressure wave, as depicted in FIG. 6A. The pre-ejection time (PEP) is defined as the period between onset of ventricular contraction and when the aortic valve opens, which includes excitation-contraction coupling (or electromechanical dissociation EMD) and isovolumic contractions (ICT). FIG. 6B, reproduced from T. Shishido, K. Hayashi, K. Shigemi, T. Sato, M. Sugimachi, and K. Sunagawa, "Single-beat estimation of end-systolic elastance using bilinearly approximated time-varying elastance curve.," Circulation, vol. 102, no. 16, pp. 1983-1989, October 2000, illustrates that for known left ventricular elastance, PEP can be derived by subtracting the time of end-diastolic elastance, $t_{ed}$, from the time at the end of the isovolumic contraction phase, $t_{ad}$. Left-ventricular Ejection time (LVET) then may be obtained by subtracting $t_{ad}$ from the time of end-systolic elastance, $t_{es}$. As illustrated in FIG. 6C, the sum of PEP and LVET, also referred to as the Q-Ac period, also may be derived using clinically observable data, as the time duration between the beginning of the Q-wave appearing on a patient's ECG, and the time point when the aortic valve closes, as may be determined from a heart sound detector or stethoscope.

All simulated information generated using the tuned 1-dimensional model then was discarded, except the synthetically generated values of the measurable input parameters: brSBP, brDBP, HR, cfPWV, crPWV, and Q-Ac period and the corresponding output values for cSBP, CO, Ees, CT, and Zao. The total dataset, organized in pairs of inputs and outputs, was divided into a training set and a testing set and 10-fold cross-validation was performed. In 10-fold cross validation, all subjects were randomly divided into 10 equal sets. One set was retained as a validation group to validate the methods, and the other nine sets were used as a training group to tune the parameters of the machine-learning model. This process was iterated 10 times, so that all synthetic patient groups appeared once in all validation groups. The outputs of the testing set were blinded and reserved as de facto accurate for later comparison. The synthetic data then were corrupted with random Gaussian noise in order to represent a more realistic data collection, as suggested in J. Liu, H.-M. Cheng, C. H. Chen, S. H. Sung, J. O. Hahn, and R. Mukkamala, "Patient-Specific Oscillometric Blood Pressure Measurement: Validation for Accuracy and Repeatability," IEEE® J Transl Eng Health Med, vol. 5, p. 1900110, 2017.

After generation of the synthetic dataset, a regression model was trained and tested to estimate the corresponding targets for the subject under consideration. By definition, the regressor (namely, the machine learning model) involved the following components: (i) the unknown parameters, β, (ii) the independent variables, Xi, and (iii) the dependent variable, Yi. In one preferred embodiment, the aim of the analysis was to investigate if the regressors $f_i$ can estimate the values of Ees, CT, and Zao for each subject from the input predictors (brSBP, brDBP, HR, cfPWV, crPWV, PEP, LVET), i.e., $$Y_i \approx f_i(X;\beta), i \in \{E_{es}, CT, Zao\}$$

Figure 7:
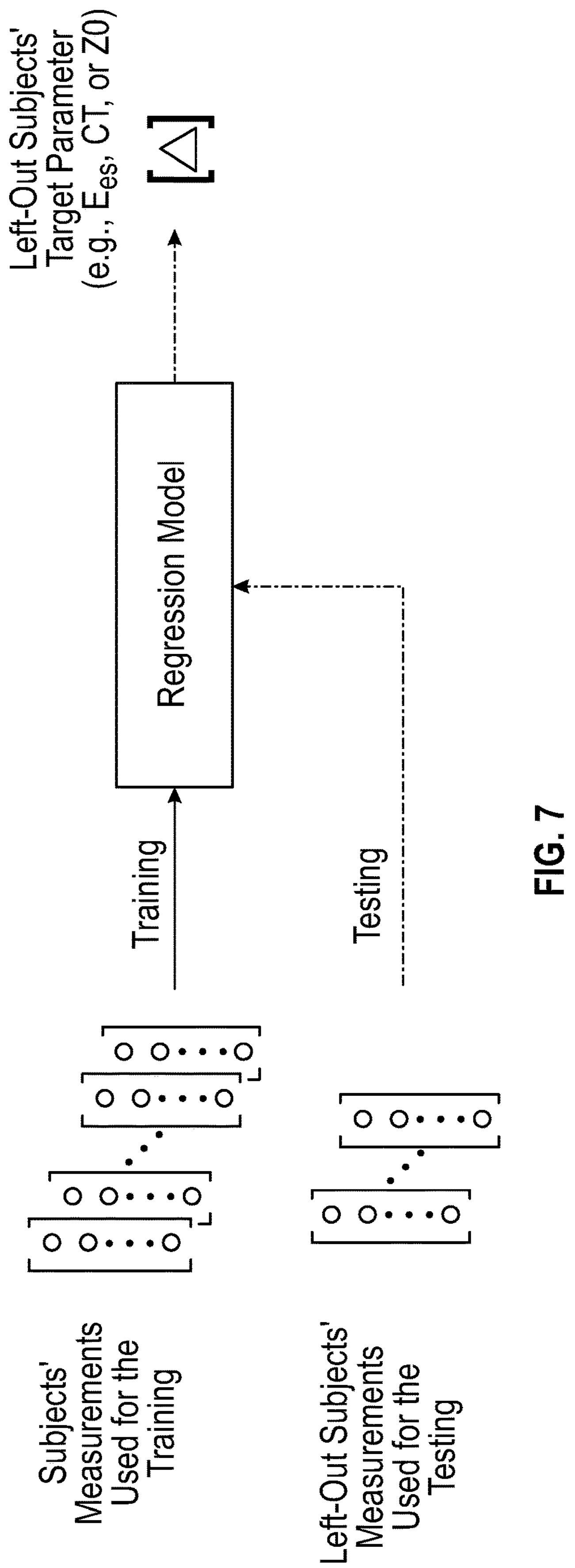
FIG. 7 is a schematic depicting how segregated data may be used train a regression model for predicting unobserved vascular parameters.

FIG. 7 schematically depicts the method in which the regression analysis was performed in an exemplary embodiment, which 9 of the 10 groups of data were used to train the regression model and the input values for the remaining tenth group was used to test the accuracy of the regression model in predicting the output values for the tenth group. Results obtained from the machine learning analysis of the data is described herein below.

End Systolic Elastance (Ees) was predicted from input values of brSBP, brDBP, HR, and the sum of PEP and LVET. As noted above, the sum of PEP and LVET may be derived clinically as the time duration between the beginning of the Q-wave (as observed on the ECG) and the time point when the aortic valve closes (as determined by the heart sound detector or stethoscope). The sum was used, as opposed to separate estimations for PEP and LVET, because the separate time periods cannot be easily derived in a real clinical setting. Regression analysis as described in J. H. Friedman, "Greedy Function Approximation: A Gradient Boosting Machine," IMS Reitz Lecture (1999), available online at statweb.stanford.edu/jhf/ftp/trebst.pdf was employed.

Figure 8A:
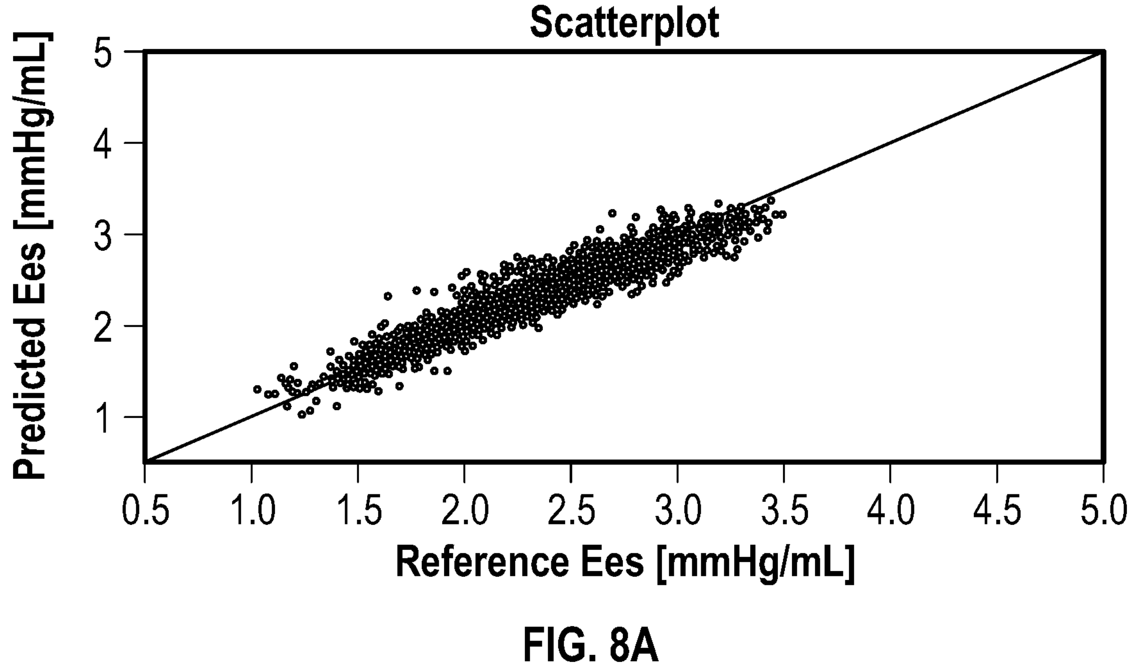
FIGS. 8A and 8B are comparisons showing performance of the inventive estimator in predicting Ees and the corresponding Bland-Altman plot.
Figure 8B:
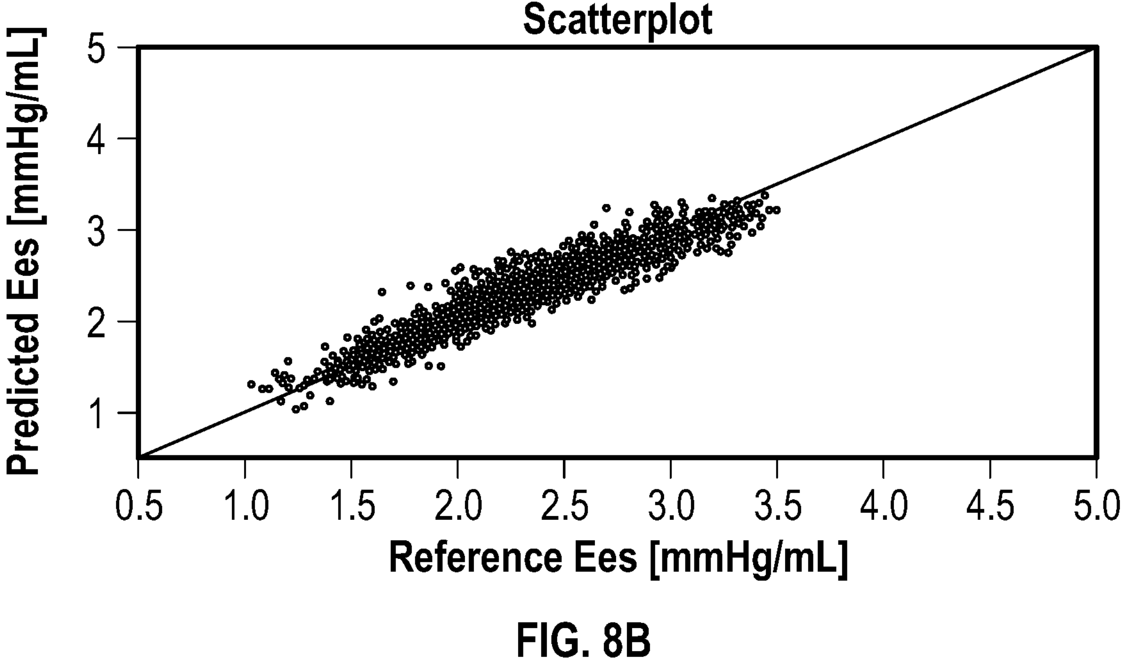

FIGS. 8A and 8B present, respectively, a comparison of the model Ees estimates to the reference Ees values and the corresponding Bland-Altman plot. Parameters of accuracy, correlation and agreement between the estimates and the actual values are shown in Table 3.

TABLE 3

| Parameter | Value |
|---|---|
| Mean difference (mmHg/mL) | −0.003 |
| Standard deviation of difference (mmHg/mL) | 0.052 |
| Normalized root mean square error (%) | 5.84 |
| Pearson's correlation coefficient | 0.95 |

Total arterial compliance (CT) and aortic input impedance (Zao) were predicted from input values for brSBP, brDBP, cfPWV, crPWV, HR, and Q-Ac period by employing regression analysis. In one embodiment, the CART machine learning algorithm described in A. Liaw and M. E. A. Wiener, "Classification and regression by randomForest," RNews 2:18-22 (2002), available online at: http://cogns-.northwestern.ed/cbmg/LiawAndWiener2002.pdf was employed.

Figure 9A:
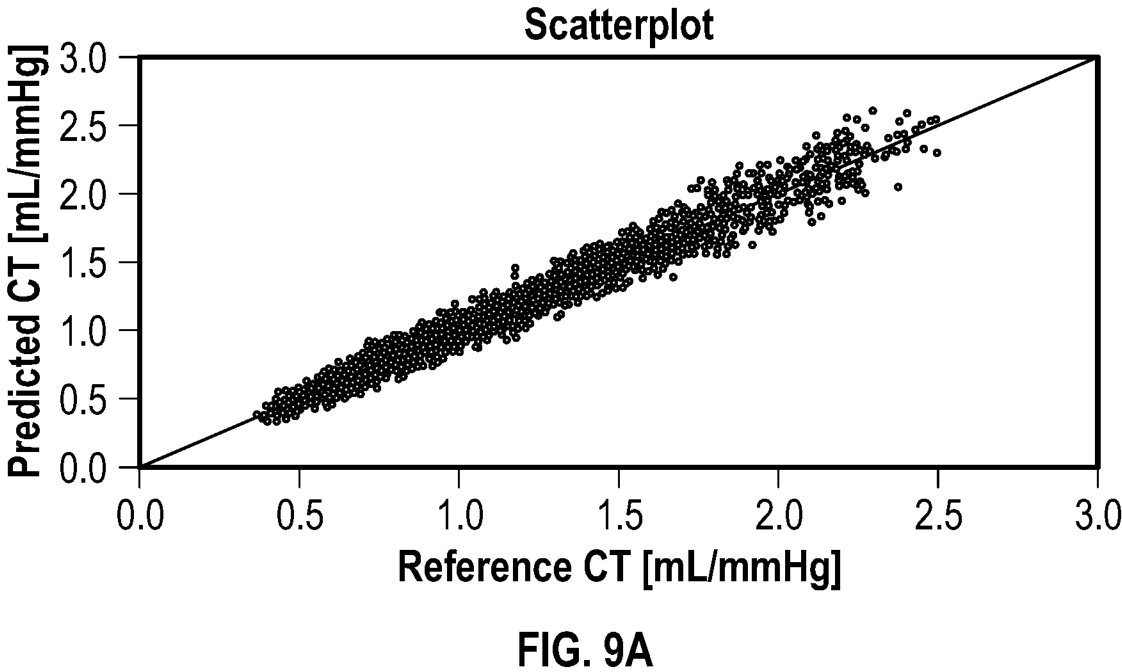
FIGS. 9A and 9B are comparisons showing performance of the inventive estimator in predicting CT and the corresponding Bland-Altman plot.
Figure 9B:
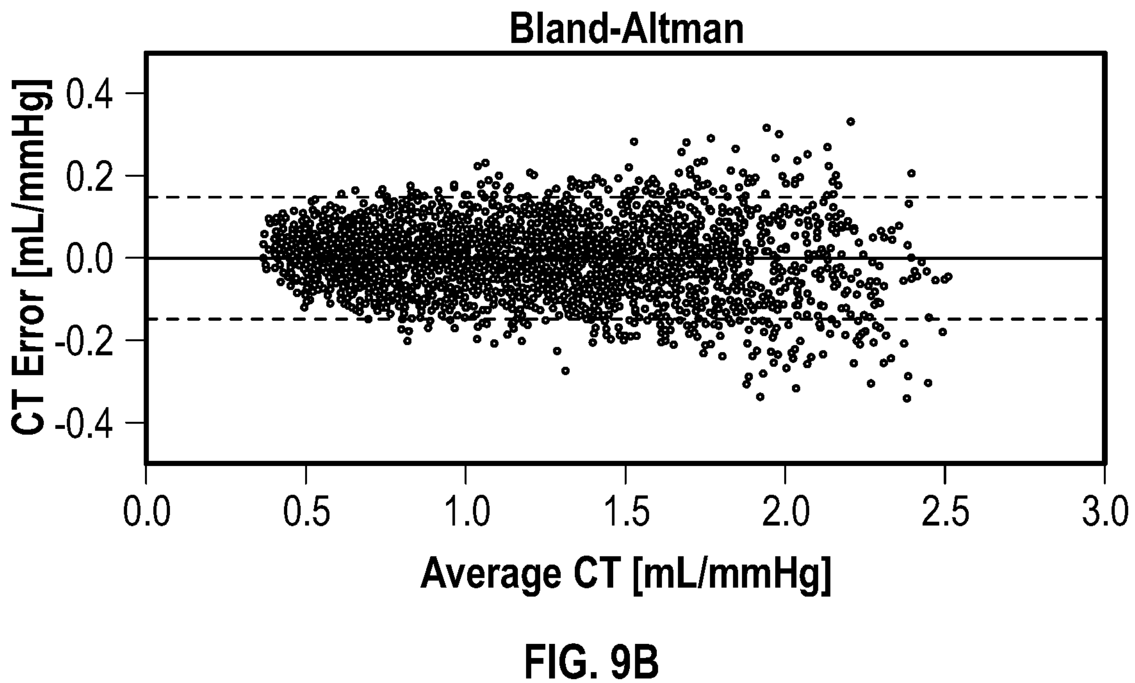

FIGS. 9A and 9B present, respectively, a comparison of the model CT estimates to the reference CT and the corresponding Bland-Altman plot. Parameters of accuracy, correlation and agreement between the estimates and the actual values are shown in Table 4.

TABLE 4

| Parameter | Value |
|---|---|
| Mean difference (mL/mmHg) | −0.0004 |
| Standard deviation of difference (mL/mmHg) | 0.076 |
| Normalized root mean square error (%) | 5.14 |
| Pearson's correlation coefficient | 0.99 |

Figure 10A:
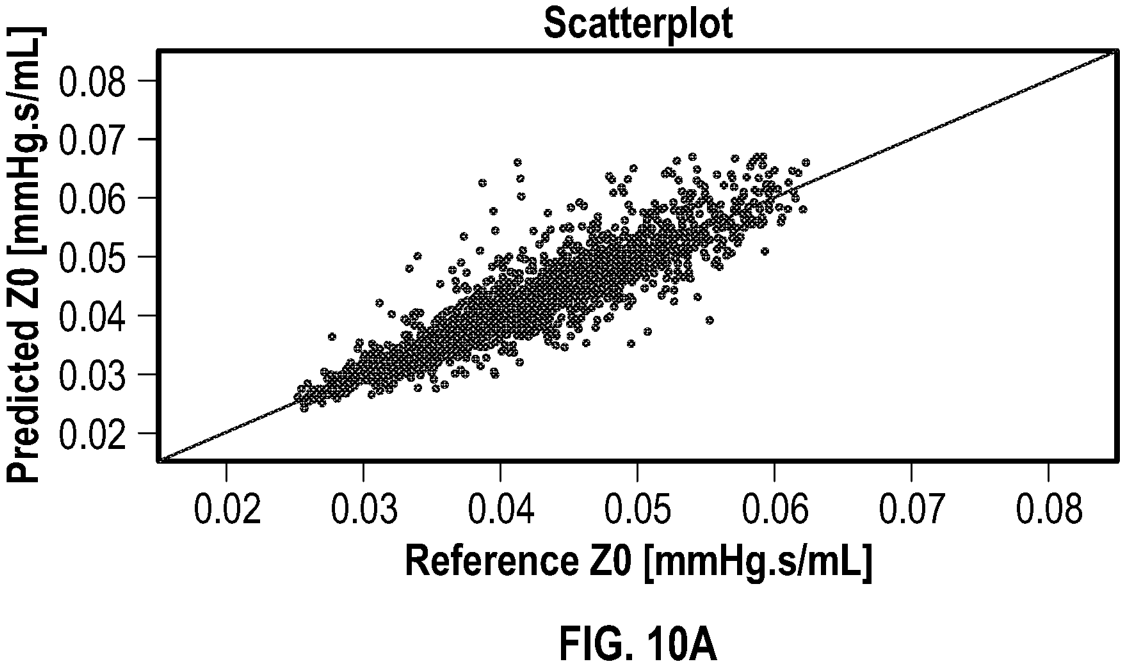
FIGS. 10A and 10B are comparisons showing performance of the inventive estimator in predicting Zao and the corresponding Bland-Altman plot.
Figure 10B:
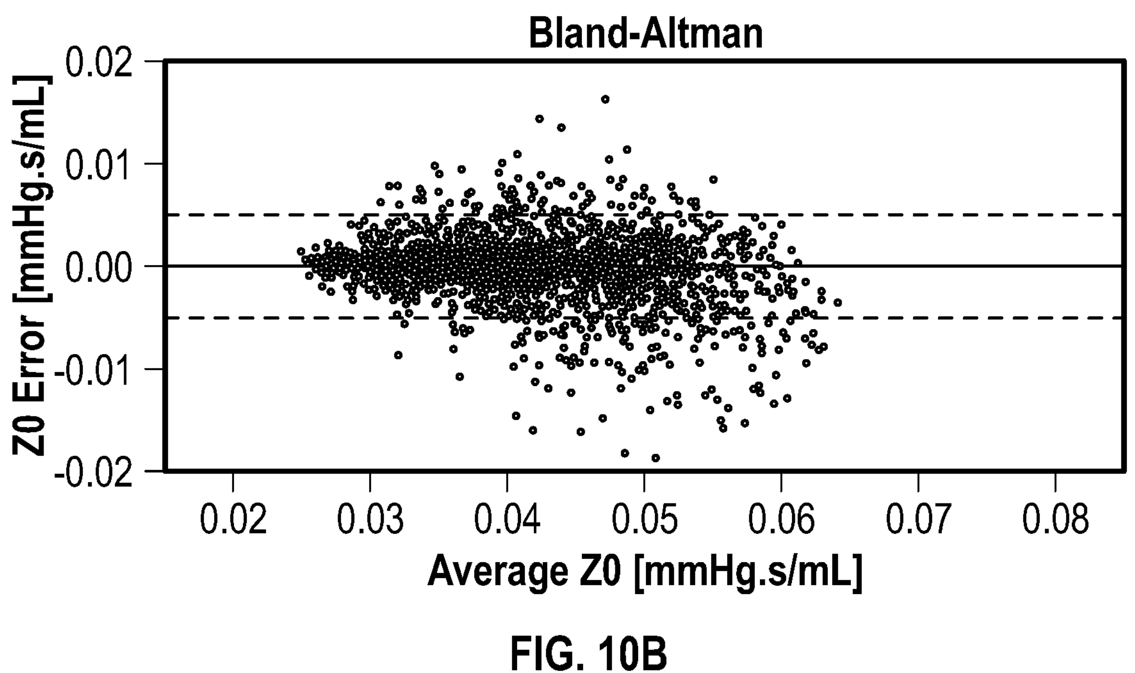

FIGS. 10A and 10B present, respectively, a comparison of the model Zao estimates to the reference Zao and the corresponding Bland-Altman plot. Parameters of accuracy, correlation and agreement between the estimates and the actual values are shown in Table 5.

TABLE 5

| Parameter | Value |
|---|---|
| Mean difference (mmHg · sec/mL) | −0.000 |
| Standard deviation of difference (mmHg · sec/mL) | 0.003 |
| Normalized root mean square error (%) | 6.49 |
| Pearson's correlation coefficient | 0.93 |

In an exemplary embodiment of the system of the present invention, the algorithm for adjusting the cardiovascular model and the machine learning models is embedded in Estimator Module 218 of console 200. The inputs required for predicting CO, cSBP, Ees, CT, and Zao, as described above, include brSBP, brDBP, HR, cfPWV, crPWV, and Q-Ac period. A conventional cuff may be used to acquire brachial pressure and HR.

CfPWV is determined from the time taken for the arterial pulse to propagate from the carotid to the femoral artery, whereas crPWV is determined from the time taken for the arterial pulse to propagate from the carotid to the radial artery. Values for cfPWV and crPWV may be computed using the outputs of three pulse sensors placed at the carotid, radial, and femoral arteries, which measure the respective arterial pulsation signals at each location. As depicted in FIG. 1, these pulse sensors may be embodied in three patches that are placed at the three arterial sites to capture signals simultaneously; the propagation times and PWVs are derived from the measured arterial pulsation signals.

Finally, the Q-AC period may be extracted using the electrocardiogram (ECG)) and an automated heart sound detector, or alternatively, a clinician using a conventional stethoscope. The heart sound detector provided the time when aortic valve closes (the second acoustic beat) with respect to the initiation of the Q-wave (observed from the ECG waveform). This data is then transmitted to console 200 running Estimator Module 218, which in turn computes CO, cSBP, Ees, CT, and Zao.

Advantageously, the system of the present invention enables the use of low-cost, readily available sensors and computer hardware with an arterial tree model of systemic circulation yields accurate estimates of CO when personalized with patient-specific noninvasive measurements of peripheral blood pressure and cf-PWV. In vivo validation of the inventive system and method demonstrates that is provides clinically acceptable estimates for CO and other key cardiovascular parameters using only patient-specific noninvasive measurements for a variety of patient conditions and age groups. As further described above, the inventive system and methods further may be augmented to provide a complete system for estimating central aortic and cardiac parameters, i.e., CO, cSBP, Ees, CT, and Zao, using inverse problem-solving techniques and machine learning models, with good accuracy and specificity for all parameters of interest.

It should be understood that the embodiments described herein are illustrative, and components may be arranged, substituted, combined, and designed in a wide variety of different configurations, all of which are contemplated and fall within the scope of this disclosure. Accordingly, the foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims.

What is claimed is:

1. A system configured to use non-invasively measurable physiologic data to estimate cardiovascular parameters of a patient that are non-invasively unobservable, the system comprising:

a plurality of pulse sensors configured to be applied to the patient, outputs of which enable computation of pulse wave velocities;

a cuff configured to measure values of systolic and diastolic blood pressures and heart rate;

a console including a processor, a display, and non-volatile storage, wherein the non-volatile storage stores instructions that, when executed by the processor:

receive the measured values of systolic and diastolic blood pressure and heart rate generated by the cuff, compute actual pulse wave velocities using the outputs of the plurality of pulse sensors;

iteratively compute estimated values of systolic and diastolic blood pressure using an arterial tree model trained to simulate hemodynamics of an atrial tree including vascular distensibility characteristics and vascular resistance characteristics and compare the estimated values of systolic and diastolic blood pressure to the measured values of systolic and diastolic blood pressure until a difference between the estimated values of systolic and diastolic blood pressure and the measured values of systolic and diastolic blood pressure are less than a first threshold, the vascular distensibility characteristics and vascular resistance characteristics of the arterial tree model adjusted with each iterative computation of the estimated values of systolic and diastolic blood pressure;

determine an estimator by iteratively computing estimated pulse wave velocities while adjusting one or more of the vascular distensibility characteristics and the vascular resistance characteristics until the difference between the estimated values of systolic and diastolic blood pressure and the measured values of systolic and diastolic blood pressure are less than the first threshold, and a difference between the estimated pulse wave velocities and the actual pulse wave velocities is less than a second threshold to thereby determine one or more of a vascular distensibility characteristic value and a vascular resistance characteristic value causing the difference between the estimated values of systolic and diastolic blood pressure and the measured values of systolic and diastolic blood pressure to be less than the first threshold and further causing the difference between the estimated pulse wave velocities and the actual pulse wave velocities to be less than the second threshold, the estimator comprising a two-layer optimization algorithm adapted to personalize the arterial tree model for the patient; and compute estimated values of cardiac output or aortic (central) systolic blood pressure using the estimator calibrated with the one or more of the vascular distensibility characteristic value and the vascular resistance characteristic value, and based on second measured values of systolic and diastolic blood pressure and second actual pulse wave velocities; and display the estimated values of cardiac output or aortic (central) systolic blood pressure on the console.

2. The system of claim 1, wherein the console is configured to determine the estimator by also adjusting a stroke volume while iteratively computing the estimated pulse wave velocities.

3. The system of claim 1, wherein the non-invasively measurable physiologic data comprises data collected from a single patient.

4. The system of claim 1, wherein the non-invasively measurable physiologic data comprises in-vivo clinical data collected from a representative patient population.

5. The system of claim 4, wherein the non-invasively measurable physiologic data further comprises a database of synthetically generated data.

6. The system of claim 4, wherein the console is configured to accept as inputs ECG waveform timing data and heart sound time data and correlate the ECG waveform timing data and heart sound time data to detector to compute left ventricular end-systolic elastance.

7. The system of claim 6, wherein the estimator is further used to compute in real time an estimated value of at least one of left ventricular end-systolic elastance, total arterial compliance and aortic impedance.

8. The system of claim 1, wherein the cuff is configured to measure brachial systolic and diastolic blood pressures.

9. The system of claim 1, wherein a first one of the plurality of sensors is disposed on a patch configured to be disposed on skin of the patient in a vicinity of a proximal arterial site and a second one of the plurality of sensors is disposed on a patch configured to be disposed on skin of the patient in a vicinity of a distal arterial site.

10. The system of claim 1, wherein the console is configured to compute actual pulse wave velocities by determining a propagation time of an arterial pulse from a carotid artery of the patient to a femoral artery of the patient.

* * * * *